United States Patent
Sato

(10) Patent No.: US 10,085,656 B2
(45) Date of Patent: Oct. 2, 2018

(54) MEASUREMENT DEVICE, MEASUREMENT METHOD, PROGRAM AND RECORDING MEDIUM

(71) Applicant: Sony Corporation, Tokyo (JP)

(72) Inventor: Hideo Sato, Tokyo (JP)

(73) Assignee: Sony Corporation (JP)

( * ) Notice: Subject to any disclaimer, the term of this patent is extended or adjusted under 35 U.S.C. 154(b) by 269 days.

(21) Appl. No.: 14/362,185

(22) PCT Filed: Nov. 16, 2012

(86) PCT No.: PCT/JP2012/079812
§ 371 (c)(1),
(2) Date: Jun. 2, 2014

(87) PCT Pub. No.: WO2013/084698
PCT Pub. Date: Jun. 13, 2013

(65) Prior Publication Data
US 2014/0343383 A1    Nov. 20, 2014

(30) Foreign Application Priority Data

Dec. 9, 2011   (JP) ................. 2011-270641

(51) Int. Cl.
*A61B 5/1455*    (2006.01)
*A61B 5/024*    (2006.01)
(Continued)

(52) U.S. Cl.
CPC ...... *A61B 5/02416* (2013.01); *A61B 5/14551* (2013.01); *A61B 5/14552* (2013.01);
(Continued)

(58) Field of Classification Search
None
See application file for complete search history.

(56) References Cited

U.S. PATENT DOCUMENTS 5,893,364 A * 4/1999 Haar ............... A61B 5/0059
356/338
2009/0147096 A1* 6/2009 Yamaguchi ...... A61B 1/00009
348/222.1

(Continued)

FOREIGN PATENT DOCUMENTS

JP    2003-135434 A    5/2003
JP    2010-125260 A    6/2010
JP    2011-022860 A    2/2011

OTHER PUBLICATIONS

International Search Report from International Publication PCT/JP2012/079812 dated Feb. 5, 2013.

*Primary Examiner* — Eric Winakur
*Assistant Examiner* — Marjan Fardanesh
(74) *Attorney, Agent, or Firm* — Lerner, David, Littenberg, Krumholz & Mentlik, LLP

(57) ABSTRACT

A measurement device according to the present disclosure includes a light source which emits at least one kind of measurement light belonging to a predetermined wavelength band toward a measurement region formed of at least part of a living body, a detection unit in which a plurality of sensors is regularly arranged in a predetermined arrangement and which detects the measurement light emitted from the light source and passing through the living body with the plurality of sensors, and an analysis unit which performs analysis processing of specifying a measurement position for measuring information on pulsation along with activities of the living body from the measurement region based on a temporal change in an amount of light of the detected measurement light by use of a detection result detected by the detection unit.

9 Claims, 13 Drawing Sheets

(51) Int. Cl.
*A61B 5/00* (2006.01)
*A61B 5/021* (2006.01)

(52) U.S. Cl.
CPC ......... *A61B 5/6826* (2013.01); *A61B 5/02116* (2013.01); *A61B 2562/0233* (2013.01); *A61B 2562/046* (2013.01); *A61B 2562/185* (2013.01)

(56) References Cited

U.S. PATENT DOCUMENTS

2011/0013074 A1    1/2011   Ichimura et al.
2012/0300989 A1*   11/2012   Nakashima ........ G06K 9/00046
                                                                                     382/115

* cited by examiner $$A(\lambda) = \sum_i A_i(\lambda) + G(\lambda) = \sum_i \varepsilon_i(\lambda) C_i l_i(\lambda) + G(\lambda)$$

$$A_i(\lambda) = \sum_j \varepsilon_{ij}(\lambda) C_{ij} l_i(\lambda)$$

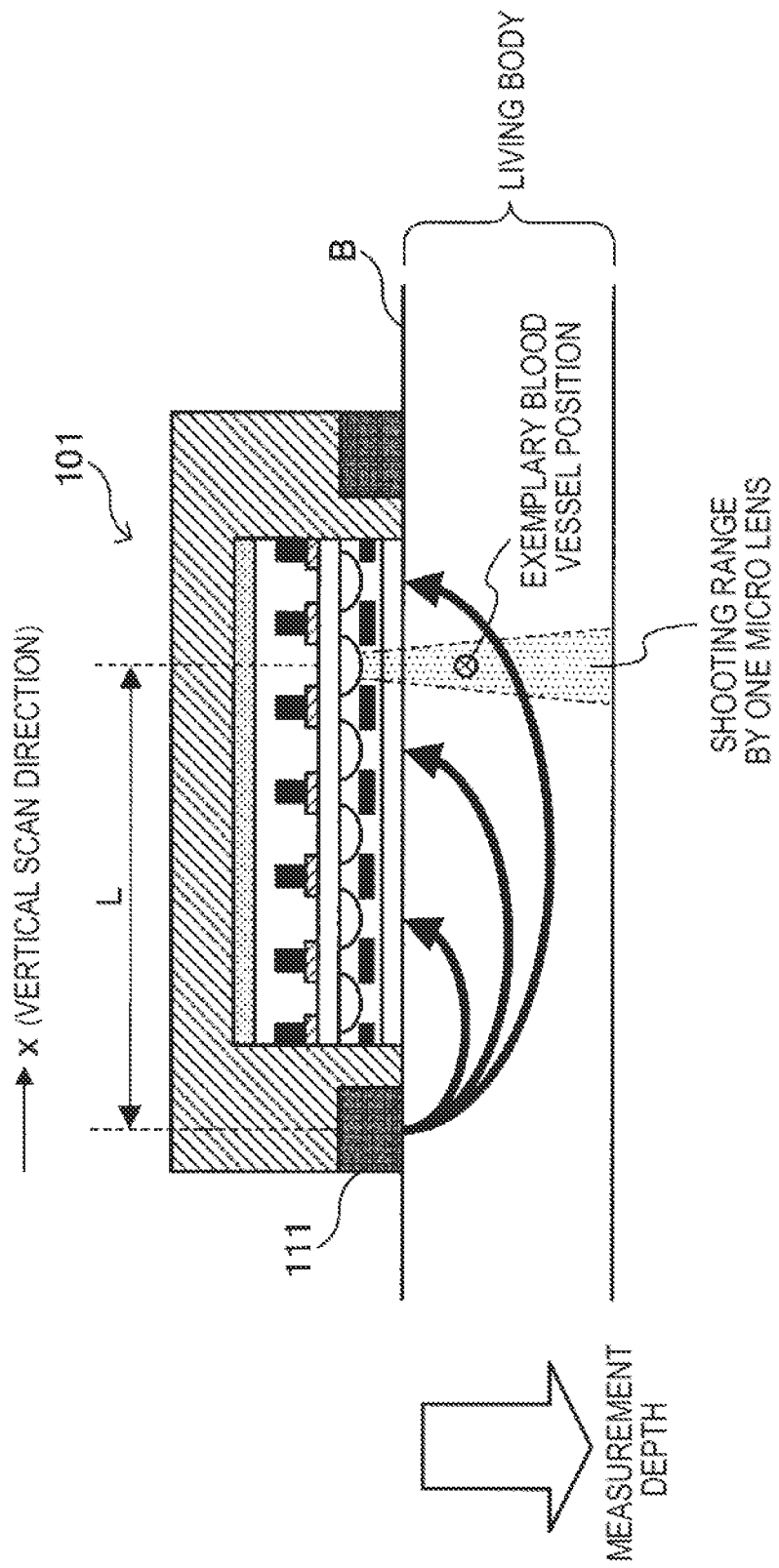

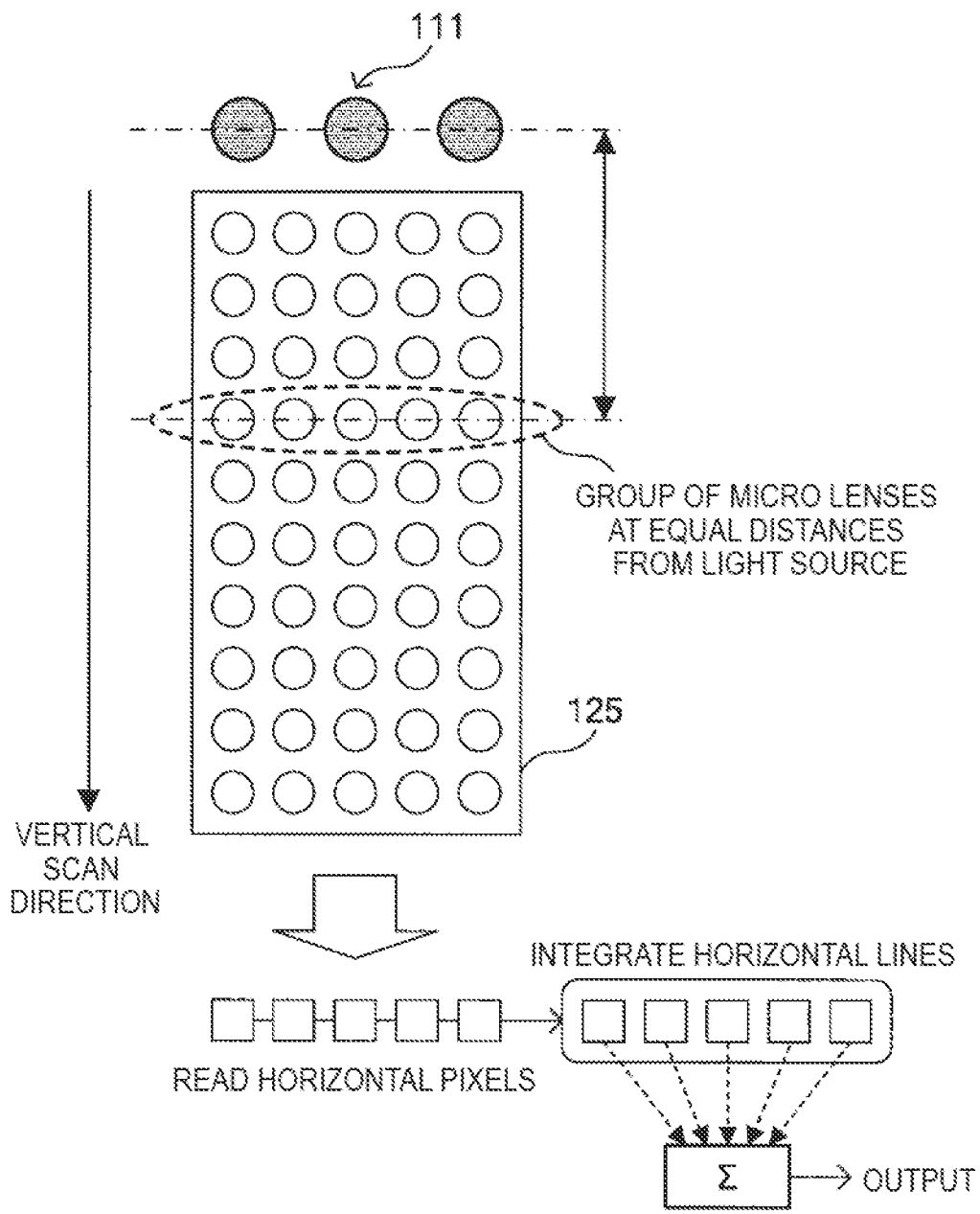

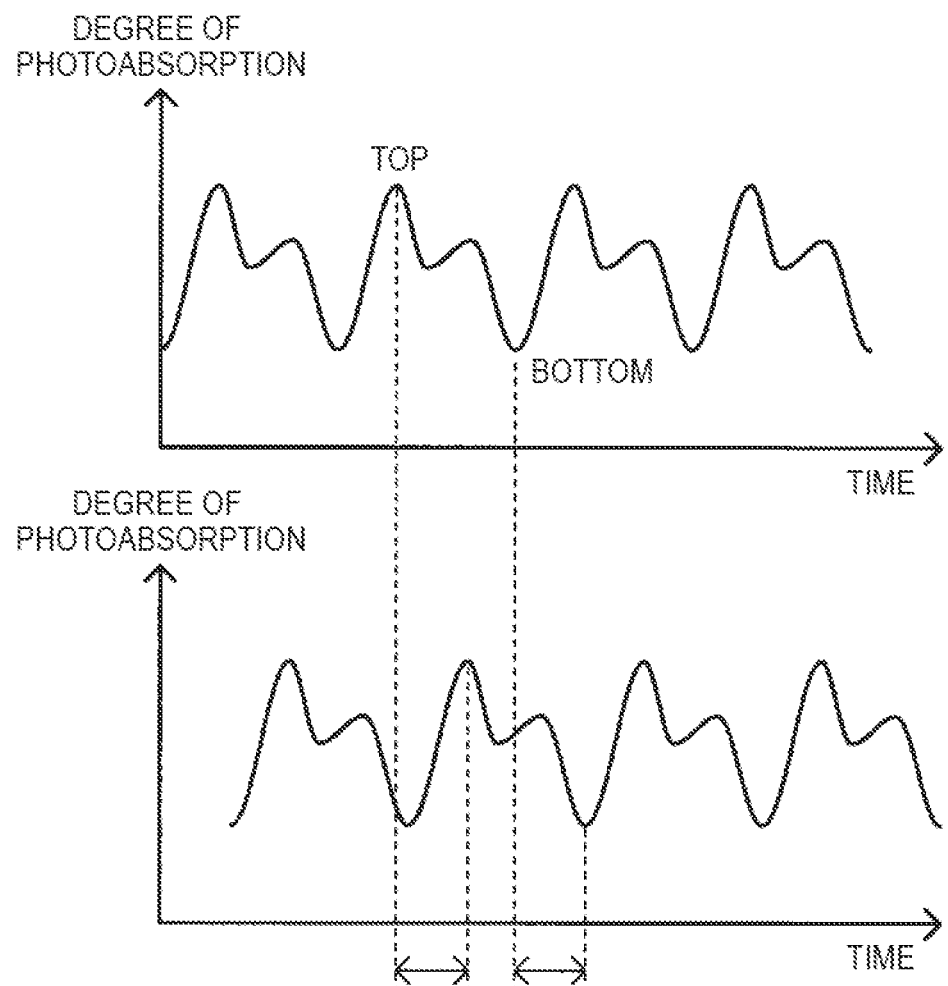

MEASUREMENT DEVICE, MEASUREMENT METHOD, PROGRAM AND RECORDING MEDIUM

CROSS-REFERENCE TO RELATED APPLICATION

The present application is a national phase entry under 35 U.S.C. § 371 of International Application No. PCT/JP2012/079812 filed Nov. 16, 2012, published on Jun. 13, 2013 as WO 2013/084698 A1, which claims priority from Japanese Patent Application No. JP 2011-270641, filed in the Japanese Patent Office on Dec. 9, 2011.

TECHNICAL FIELD

The present disclosure relates to a measurement device, a measurement method, a program and a recording medium.

BACKGROUND ART

Many techniques for measuring pulse waveforms (arterial pulsatile waveforms) are used in the field of medicine. A pulse waveform is analyzed in its shape to be used for examining a circulatory system (such as measuring a degree of arteriosclerosis or measuring stress) and to be used for pulse oximeter (arterial oxygen saturation measurement device) and the like.

Among others, a technique called photoplethysmography, which is a technique for measuring pulse waveforms in a non-invasive and percutaneous manner without blood withdrawal or puncture (See, the following Patent Literature 1, for example), is very widely used since it can easily make measurements without loads on a human body.

A pulse oximeter using photoplethysmography determines oxygen saturation based on measured pulse waveforms by use of a property that oxygenated hemoglobin absorbs infrared light (with a waveform of around 940 nm, for example) and reduction hemoglobin absorbs red light (with a waveform of around 660 nm, for example). That is, the light with the two wavelengths are irradiated on a human body to measure degrees of photoabsorption at the respective wavelengths, a relative concentration of each hemoglobin is calculated based on the resultant degrees of photoabsorption, and oxygen saturation is calculated from the resultant relative concentrations.

There are present two types of pulse oximeter using photoplethysmography including a transmissive pulse oximeter for sandwiching a finger as a site to be measured between a light source and a photo detector, and a reflective pulse oximeter in which a light source and a photo detector are arranged on either side of a site to be measured such as a finger.

CITATION LIST

Patent Literature

Patent Literature 1: JP 2003-135434A

SUMMARY OF INVENTION

Technical Problem

With the two types of pulse oximeter using photoplethysmography as described above, the transmissive type is advantageous in obtaining stable pulse waveforms, but a site to be measured needs to be tightly sandwiched in order to keep optical stability, and thus its long-time use causes loads on a user. On the other hand, the reflective pulse oximeter contacts only either side of a human body so that measurements can be made with low loads on a user, but a light efficiency is disadvantageous and thus pulse waveforms with sufficient accuracy are difficult to acquire.

Therefore, the present disclosure proposes a measurement device capable of measuring a pulse waveform with high accuracy while reducing loads on a user, a measurement method, a program and a recording medium in terms of the above circumstances.

Solution to Problem

According to the present disclosure, there is provided a measurement device including a light source which emits at least one kind of measurement light belonging to a predetermined wavelength band toward a measurement region formed of at least part of a living body, a detection unit in which a plurality of sensors is regularly arranged in a predetermined arrangement and which detects the measurement light emitted from the light source and passing through the living body with the plurality of sensors, and analysis unit which performs an analysis processing of specifying a measurement position for measuring information on pulsation along with activities of the living body from the measurement region based on a temporal change in an amount of light of the detected measurement light by use of a detection result detected by the detection unit.

Further, according to the present disclosure, there is provided a measurement method including emitting at least one kind of measurement light belonging to a predetermined wavelength band toward a measurement region formed of at least part of a living body, detecting the measurement light emitted from a light source and passing through the living body with a detection unit in which a plurality of sensors is regularly arranged in a predetermined arrangement, and performing analysis processing of specifying a measurement position for measuring information on pulsation along with activities of the living body from the measurement region based on a temporal change in an amount of light of the detected measurement light by use of a detected detection result.

Further, according to the present disclosure, there is provided a program for causing a computer communicable with a measurement device including a light source which emits at least one kind of measurement light belonging to a predetermined wavelength band toward a measurement region formed of at least part of a living body, and a detection unit in which a plurality of sensors is regularly arranged in a predetermined arrangement and which detects the measurement light emitted from the light source and passing through the living body with the plurality of sensors to achieve an analysis function of performing analysis processing of specifying a measurement position for measuring information on pulsation along with activities of the living body from the measurement region based on a temporal change in an amount of light of the detected measurement light by use of a detection result detected by the detection unit.

Further, according to the present disclosure, there is provided a recording medium recording a program therein, the program for causing a computer communicable with a measurement device including a light source which emits at least one kind of measurement light belonging to a predetermined wavelength band toward a measurement region formed of at least part of a living body, and a detection unit in which a plurality of sensors is regularly arranged in a predetermined arrangement and which detects the measurement light emitted from the light source and passing through the living body with the plurality of sensors to achieve an analysis function of performing analysis processing of specifying a measurement position for measuring information on pulsation along with activities of the living body from the measurement region based on a temporal change in an amount of light of the detected measurement light by use of a detection result detected by the detection unit.

Further, according to the present disclosure, there is provided a measurement device including a light source which emits at least one kind of measurement light belonging to a predetermined wavelength band toward a measurement region formed of at least part of a living body, a detection unit which detects the measurement light emitted from the light source and passing through the living body with a sensor including a micro lens array in which a plurality of lenses is regularly arranged in a grid shape, and an analysis unit which performs analysis processing of specifying a measurement position for measuring information on pulsation along with activities of the living body from the measurement region based on a temporal change in an amount of light of the detected measurement light by use of a detection result detected by the detection unit, and calculates a pulse waveform derived from arterial pulsation inside the living body corresponding to the measurement region.

Further, according to the present disclosure, there is provided a measurement method including emitting at least one kind of measurement light belonging to a predetermined wavelength band toward a measurement region formed of at least part of a living body, detecting the measurement light emitted from a light source and passing through the living body with a sensor including a micro lens array in which a plurality of lenses is regularly arranged in a grid shape, and performing analysis processing of specifying a measurement position for measuring information on pulsation along with activities of the living body from the measurement region based on a temporal change in an amount of light of the detected measurement light by use of a detected detection result, and calculating a pulse waveform derived from arterial pulsation inside the living body corresponding to the measurement region as information on pulsation along with activities of the living body based on a temporal change in the amount of light of the measurement light.

According to the present disclosure, at least one kind of measurement light belonging to a predetermined wavelength band is emitted toward a measurement region made of at least part of a living body, the measurement light emitted from the light source and passing through the living body is detected by the sensor in which a plurality of sensors are regularly arranged in a predetermined arrangement, and a measurement position for measuring information on pulsation along with activities of the living body is specified from the measurement region based on a temporal change in the amount of light of the detected measurement light by use of a detected detection result.

Advantageous Effects of Invention

According to the present disclosure described above, it is possible to measure pulse waveforms with high accuracy while reducing loads on a user.

BRIEF DESCRIPTION OF DRAWINGS

FIG. 9 is an explanatory diagram illustrating the exemplary measurement unit provided in the measurement device according to the embodiment;

FIG. 11 is an explanatory diagram for explaining the measurement device according to the embodiment;

FIG. 12 is an explanatory diagram for explaining the measurement device according to the embodiment.

DESCRIPTION OF EMBODIMENTS

Hereinafter, preferred embodiment of the present disclosure will be described in detail with reference to the appended drawings. Note that, in this specification and the drawings, elements that have substantially the same function and structure are denoted with the same reference signs, and repeated explanation is omitted.

The explanation will be made in the following order.
(1) Human body's skin structure model
(2) Principle of pulse oximeter
(3) First embodiment
(4) Hardware structure of measurement device according to embodiment of present disclosure
(5) Conclusion
(Human Body's Skin Structure Model)

Figure 1:
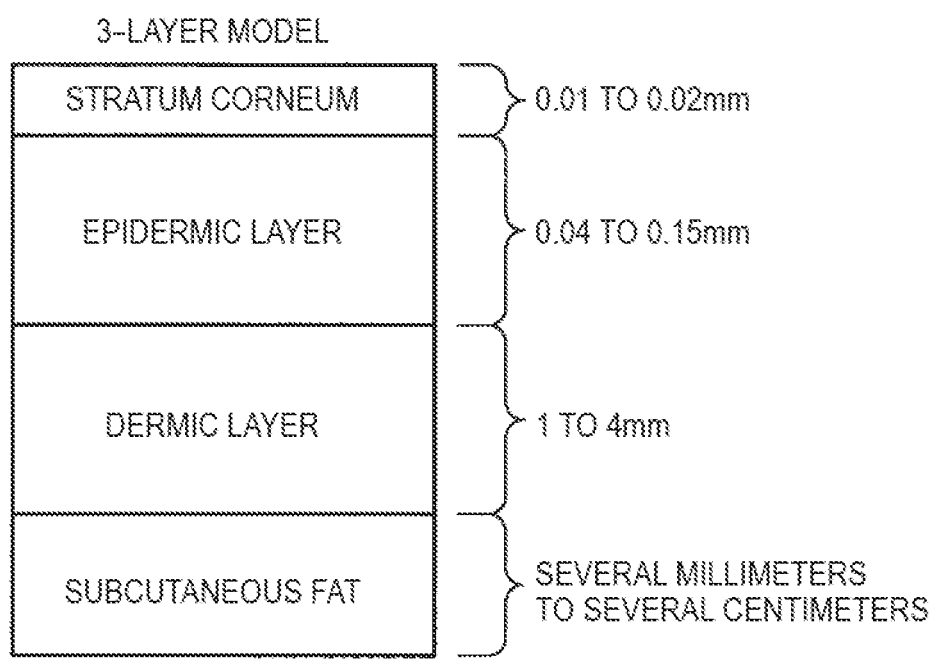
FIG. 1 is an explanatory diagram illustrating an exemplary human body's skin structure model.

A skin structure model as a modeled human body's skin structure will be briefly described with reference to FIG. 1 prior to describing a measurement device, a measurement method, a program and a recording medium according to the embodiment of the present disclosure. FIG. 1 is an explanatory diagram illustrating an exemplary human body's skin structure model.

As described above, there has been developed a technique for measuring blood and body fluid components such as glucose, albumin, AGEs (Advanced Glycation Endproducts), cholesterol, and oxygenated/reduction hemoglobin present in a human body with non-invasive optical measurement.

How a human body's skin structure is modeled is important for analyzing measured data. An exemplary human body's skin structure model is a 3-layer model as illustrated in FIG. 1.

The 3-layer model illustrated in FIG. 1 is such that subcutaneous tissues below the stratum corneum of the skin are modelled into the three layers of epidermic layer, dermic layer and subcutaneous fat. In the 3-layer model, though depending on a person, the stratum corneum is equivalent to about 0.01 to 0.02 mm inward from the body surface, the epidermic layer is equivalent to about 0.04 to 0.15 mm from the body surface, the dermic layer is equivalent to about 1 to 4 mm from the body surface, and the subcutaneous fat is equivalent to about several millimeters to several centimeters from the body surface.

In the skin structure, capillaries are present in the dermic layer, various blood components such as oxygenated hemoglobin and reduction hemoglobin are present in the capillaries, and fat cells are mainly present in the subcutaneous fat. Thus, a skin structure model to be taken into consideration is important for measuring the components with non-invasive optical measurement.

However, the human body's skin structure, or various components contained in the skin structure vary depending on an over-time change of a person to be measured, obesity, suntan, racial difference, sex, constitution, and the like, and largely depends on personal characteristics. Thus, non-invasive measurement of a component in the body based on the skin structure model is strongly influenced by a variation in the skin structure model illustrated in FIG. 1.

Therefore, it is preferable to specify a proper detection position and to detect pulse waveforms at the specified detection position in each person to be measured in order to detect pulse waveforms caused by arterial pulsation with high accuracy. Thus, the present inventors have eagerly studied a technique capable of measuring pulse waveforms with high accuracy while reducing loads on a user in terms of the above circumstances. Consequently, the present inventors have achieved a measurement device and a measurement method according to the embodiment of the present disclosure described below.

(Principle of Pulse Oximeter)

Figure 2A:
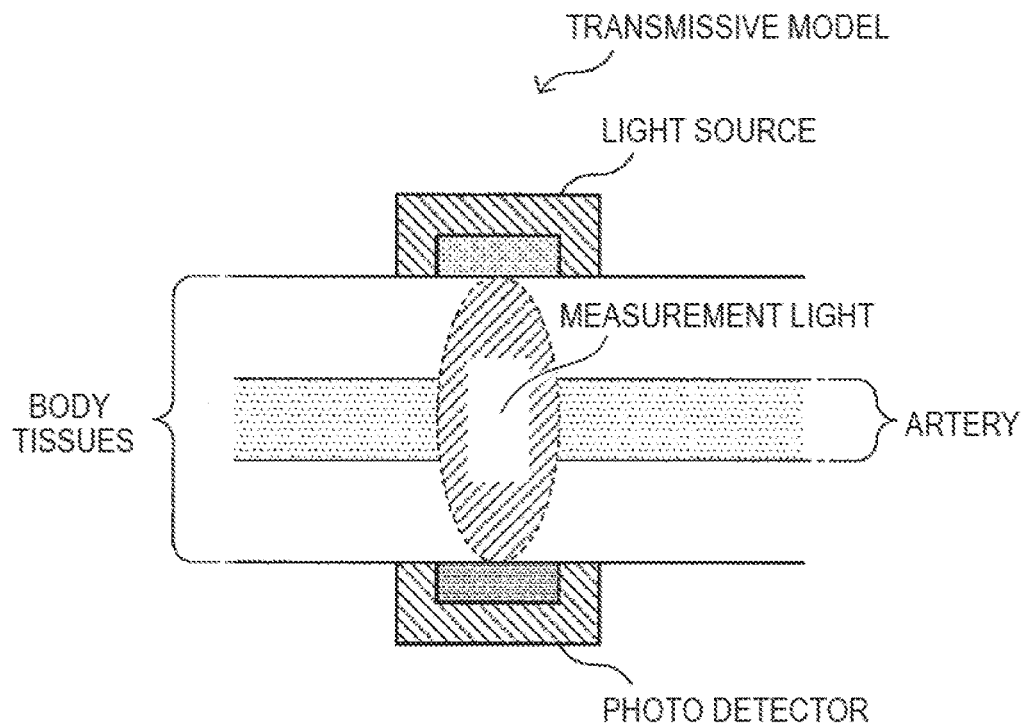
FIG. 2A is an explanatory diagram illustrating a structure of a general pulse oximeter.
Figure 2B:
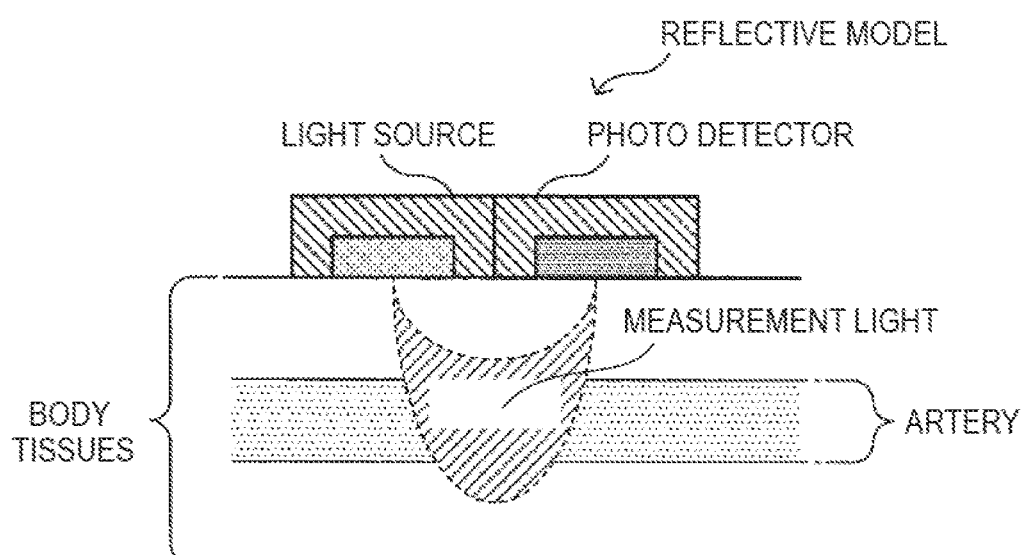
FIG. 2B is an explanatory diagram illustrating a structure of a general pulse oximeter.
Figure 3:
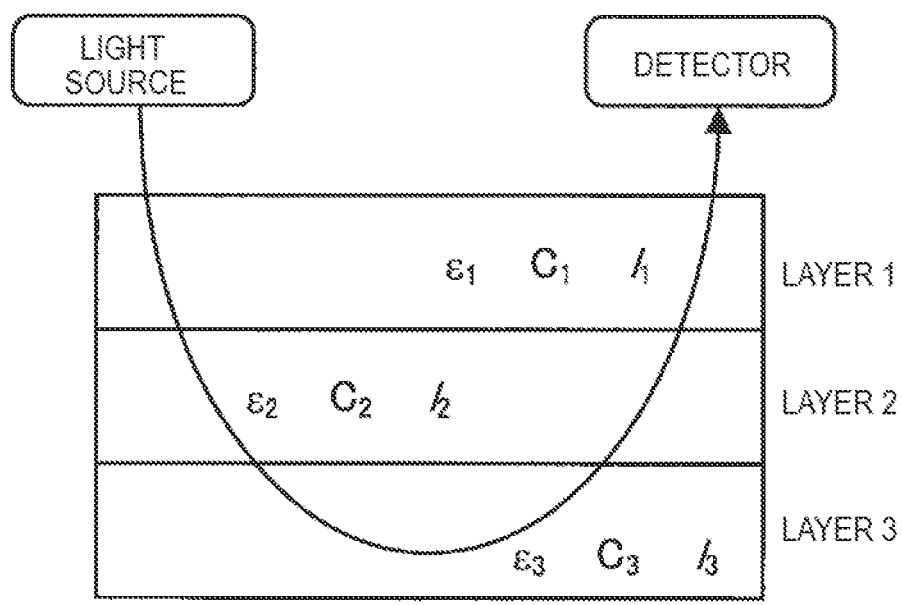
FIG. 3 is an explanatory diagram for explaining the extended Lambert-Beer law.

Subsequently, general pulse oximeters using photoplethysmography will be briefly described with reference to FIG. 2A, FIG. 2B and FIG. 3 prior to explaining a measurement device, a measurement method, a program and a recording medium according to the embodiment of the present disclosure. FIG. 2A and FIG. 2B are the explanatory diagrams illustrating the structures of the general pulse oximeters. FIG. 3 is an explanatory diagram for explaining the extended Lambert-Beer law.

The pulse oximeter is a device for measuring percutaneous oxygen saturation (called SpO2). The pulse oximeter includes a general pulse waveform measurement device as a component.

In the pulse oximeter, a photoabsorption degree measurement unit connected with a measurement probe measures biological information. The measurement probe is configured of a light source and a photo detector as illustrated in FIG. 2A and FIG. 2B, and is directed for measuring a temporal change of photoabsorption by a living body. A measurement result on photoabsorption measured by the measurement probe is output to a frequency filter, and a frequency component resulting from arterial pulsation (which will be simply denoted as "pulsation component" below) is separated in the frequency filter. Thereafter, oxygen saturation is calculated based on amplitude of the separated pulsation component. The calculated oxygen saturation is output to the user.

In the pulse oximeter, light with a plurality of wavelengths needs to be used for light (incident light) to be irradiated toward a living body. Thus, a plurality of light sources is arranged in the measurement probe, and is switched for use in a time division manner. Light with a wavelength belonging to a band from red light to near-infrared light is used for the incident light in many cases since it easily reaches the inside of the living body.

With the measurement probe in the pulse oximeter, as illustrated in FIG. 2A and FIG. 2B, incident light is irradiated on the skin surface of the living body from the light source, and exit light emitted from the living body after reflection or diffusion in the living body is detected by the photo detector. In the transmissive pulse oximeter illustrated in FIG. 2A, the light source and the photo detector are provide to be mutually opposed across part of the living body (such as finger), and the photo detector detects an exit light passing through the living body while diffusing therein. In the reflective pulse oximeter illustrated in FIG. 2B, the light source and the photo detector are arranged on the same side of part of the living body, and exit light propagating substantially in a U shape after reflection or diffusion in the living body is detected by the photo detector. At this time, the incident light is partially absorbed in arteries, veins or other body tissues present in the living body, and is to be observed as the exit light.

The pulse oximeter utilizes the extended Lambert-Beer law in order to associate measured actual data with the amount of photoabsorption due to an in vivo component of interest (or oxygenated hemoglobin or reduction hemoglobin). The pulse oximeter takes into consideration propagation of light inside a living body in terms of a living body, or an object (light scattering body) for diffusing light, and thus the general Lambert-Beer law which does not take into consideration the scattering/diffusing effects cannot be used. Thus, the pulse oximeter utilizes the extended Lambert-Beer law indicated in the following Equation 11, thereby to analyze resultant measurement data. The extended Lambert-Beer law will be briefly described below with reference to FIG. 3.

[Math. 1]

$$A(\lambda) = -\log\frac{I(\lambda)}{I_0(\lambda)} = \sum_i A_i(\lambda) + G(\lambda) = \sum_i \varepsilon_i(\lambda)C_i l_i(\lambda) + G(\lambda) \quad \text{Equation 11}$$

where, in the above Equation 11, $\lambda$: Wavelength of light of interest, $A(\lambda)$: Degree of photoabsorption with wavelength $\lambda$, $I_0(\lambda)$: Intensity of light with wavelength $\lambda$ incident into scattering body, $I(\lambda)$: Detection intensity of light with wavelength $\lambda$ passing through scattering body, $G(\lambda)$: Amount of attenuation due to scattering of light with wavelength $\lambda$, and $\varepsilon_i(\lambda)$: Photoabsorption coefficient of light with wavelength $\lambda$ in substance i, which is specific to substance.

$C_i$: Concentration of substance i, and $I_i$: Average optical path length when light with wavelength $\lambda$ propagates in substance i.

There will be assumed herein that the extended Lambert-Beer law is applied to a scattering body having a layer structure as illustrated in FIG. 3. In the following, a subscript for specifying a layer is described as i and the number of substances contained in a layer i is indicated with a subscript j. The extended Lambert-Beer law for the scattering body having the layer structure as illustrated in FIG. 3 can be expressed in the following Equation 12 and Equation 13.

[Math. 2]

$$A(\lambda) = -\log\frac{I(\lambda)}{I_0(\lambda)} = \sum_i A_i(\lambda) + G(\lambda) = \sum_i \varepsilon_i(\lambda)C_i l_i(\lambda) + G(\lambda) \quad \text{(Equation 12)}$$

$$A_i(\lambda) = \sum_j \varepsilon_{ij}(\lambda)C_{ij}l_i(\lambda) \quad \text{(Equation 13)}$$

where, in the Equation 12 and Equation 13,
$\lambda$: Wavelength of light of interest,
$A(\lambda)$: Degree of photoabsorption with wavelength $\lambda$,
$I_0(\lambda)$: Intensity of light with wavelength $\lambda$ incident into scattering body,
$I(\lambda)$: Detection intensity of light with wavelength $\lambda$ passing through scattering body,
$G(\lambda)$: Amount of attenuation due to scattering of light with wavelength $\lambda$,
$\varepsilon_i(\lambda)$: Photoabsorption coefficient of light with wavelength $\lambda$ in layer i,
$C_i$: Concentration of substance contained in layer i,
$l_i$: Average optical path length when light with wavelength $\lambda$ propagates in layer i,
$\varepsilon_{ij}(\lambda)$: Photoabsorption coefficient of light with wavelength $\lambda$ in substance j contained in layer i, and
$C_{ij}$: Concentration of substance j contained in layer i.

Herein, a photoabsorption coefficient of an in vivo component of interest can be specified by previously measuring an absorption spectrum of the in vivo component of interest or acquiring data from a well-known database. Thus, the photoabsorption coefficient of the in vivo component of interest can be handled as the known amount by use of the data. The leftmost side in the Equation 12 is actual measurement data on each wavelength measured by the pulse oximeter.

Figure 4:
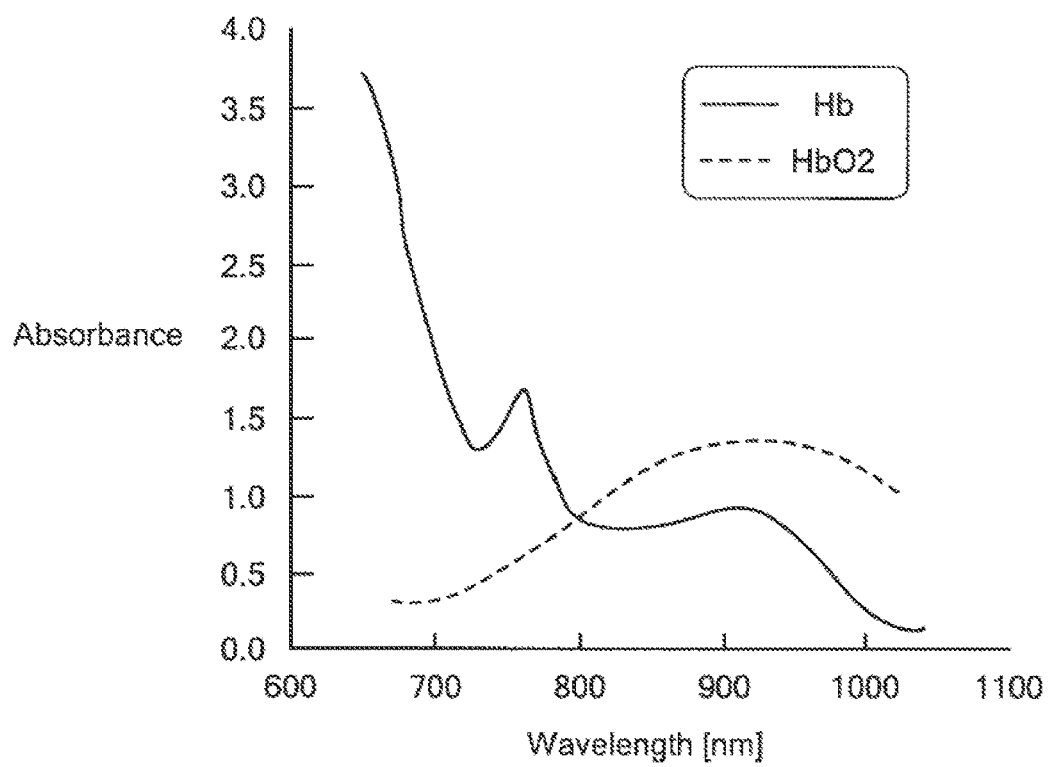
FIG. 4 is a graph illustrating exemplary photoabsorption spectra of oxygenated hemoglobin and reduction hemoglobin.

For hemoglobin in the blood of interest in the pulse oximeter, a degree of photoabsorption changes due to the presence of a bond with oxygen and the degree of photoabsorption is different depending on a wavelength to be observed as illustrated in FIG. 4. Therefore, the degrees of photoabsorption are measured at a plurality of wavelengths thereby to find a ratio between reduction hemoglobin (Hb) not bound with oxygen and oxygenated hemoglobin (HbO2).

A rate of oxygenated hemoglobin in the total hemoglobin contained in the blood is called blood oxygen saturation. Arterial oxygen saturation SaO2 is particularly helpful for biological information, and the oxygen saturation SaO2 can be calculated in the following Equation 14. SpO2 described above is percutaneously-measured SaO2.

[Math. 3]

$$SaO_2 = \frac{C_{HbO2}}{C_{HbO2} + C_{Hb}} \quad \text{Equation 14}$$

In the Equation 14,
SaO2: Arterial oxygen saturation,
$C_{HbO2}$: Concentration of oxygenated hemoglobin, and
$C_{Hb}$: Concentration of reduction hemoglobin.

As stated above, the exit light detected by the photo detector of the measurement probe in the pulse oximeter is absorbed in the body tissues or blood components in a reflecting/scattering progress of the incident light in the body. An intensity of the exit light is analyzed thereby to calculate SpO2, but SpO2 is arterial oxygen saturation, and thus an effect of photoabsorption due to any other than arterial blood is needed to be excluded from the exit light.

Figure 5:
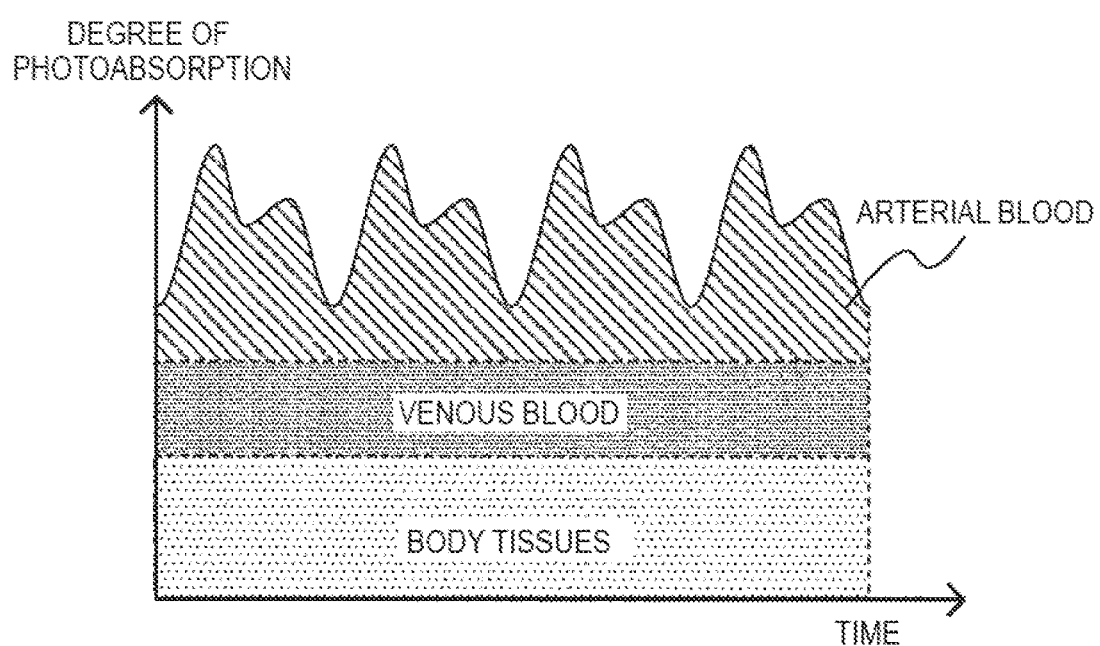
FIG. 5 is an explanatory diagram illustrating relationships between living body's skin tissues and degrees of photoabsorption.

The elements causing photoabsorption of incident light can be largely classified into three types such as arterial blood, venous blood and other body tissues as illustrated in FIG. 5. At this time, the exit light is subjected to photoabsorption as indicated in the following Equation 15.

[Math. 4]

$$OD^\lambda = \log\left(\frac{I_0^\lambda}{I^\lambda}\right) = \varepsilon_t^\lambda C_t d_t + \varepsilon_v^\lambda C_v d_v + (\varepsilon_{Hb}^\lambda C_{Hb} + \varepsilon_{HbO2}^\lambda C_{HbO2})d_a + B_S \quad \text{Equation 15}$$

In the Equation 15,
$\lambda$: Wavelength,
$\varepsilon$: Photoabsorption coefficient,
C: Concentration, and
d: Optical path length.

In the Equation 15, the first term in the rightmost side indicates photoabsorption caused by a component other than blood, the second term in the rightmost side indicates photoabsorption caused by venous blood, the third term in the rightmost side indicates photoabsorption caused by arterial blood, and the fourth term in the rightmost side indicates photoabsorption caused by diffusion in the living body.

The pulse oximeter uses the fact that pulsation is observed only in the arteries among the three elements, and separates photoabsorption of the arterial blood from other elements. That is, the Equation 15 is temporally differentiated thereby to remove an effect of photoabsorption due to veins and other body tissues having no pulsation (or no temporal change). The differentiation operation corresponds to removal of a DC component by the frequency filter in a signal processing, and is none other than a pulse waveform extraction processing.

In the Equation 14, two unknown numbers for calculating SaO2 are the reduction hemoglobin concentration ($C_{Hb}$) and the oxygenated hemoglobin concentration ($C_{HbO2}$), and thus two measurement results need to be simultaneously obtained in order to specify the two unknown numbers. Thus, the pulse oximeter uses at least two wavelengths to make measurements.

There will be assumed below a case in which measurements are made by two kinds of incident light with wavelengths $\lambda 1$ and $\lambda 2$ and temporal changes $\Delta OD^{\lambda,1}$ and $\Delta OD^{\lambda,2}$ of the intensities of the exit light are found. In this case, the temporal changes of the intensities of the exit light measured by the two wavelengths can be expressed in the following Equation 16 from the equation 15. Thus, the unknown hemoglobin concentration ($C_{Hb}$) and oxygenated hemoglobin concentration ($C_{HbO2}$) can be calculated as in the following Equation 17 by use of the photoabsorption coefficients of hemoglobin and oxygenated hemoglobin, and the measurement results.

[Math. 5]

$$\begin{bmatrix} \varepsilon_{Hb}^{\lambda 1} & \varepsilon_{HbO2}^{\lambda 1} \\ \varepsilon_{Hb}^{\lambda 2} & \varepsilon_{HbO2}^{\lambda 2} \end{bmatrix} \begin{bmatrix} C_{Hb} \\ H_{HbO2} \end{bmatrix} = \frac{1}{\Delta d_a} \begin{bmatrix} \Delta OD^{\lambda 1} \\ \Delta OD^{\lambda 2} \end{bmatrix} \quad \text{(Equation 16)}$$

$$\begin{bmatrix} C_{Hb} \\ C_{HbO2} \end{bmatrix} = \frac{1}{\Delta d_a} \begin{bmatrix} \varepsilon_{Hb}^{\lambda 1} & \varepsilon_{HbO2}^{\lambda 1} \\ \varepsilon_{Hb}^{\lambda 2} & \varepsilon_{HbO2}^{\lambda 2} \end{bmatrix}^{-1} \begin{bmatrix} \Delta OD^{\lambda 1} \\ \Delta OD^{\lambda 2} \end{bmatrix} \quad \text{(Equation 17)}$$

Therefore, when the Equation 17 is substituted into the Equation 14, the following Equation 18 is obtained. In the following Equation 18, the parameters α, β, and Φ are as in the following Equations 19a to 19c.

[Math. 6]

$$\begin{aligned} SaO_2 &= \frac{C_{HbO2}}{C_{HbO2} + C_{Hb}} \quad \text{(Equation 18)} \\ &= \frac{\varepsilon_{Hb}^{\lambda 1} \Delta OD^{\lambda 2} - \varepsilon_{Hb}^{\lambda 2} \Delta OD^{\lambda 1}}{\varepsilon_{HbO2}^{\lambda 1} \Delta OD^{\lambda 2} - \varepsilon_{HbO2}^{\lambda 2} \Delta OD^{\lambda 1}} \\ &= \alpha + \beta \cdot \frac{\Delta OD^{\lambda 1}}{\Delta OD^{\lambda 2}} \\ &= \alpha + \beta \cdot \Phi \end{aligned}$$

$$\alpha = \frac{\varepsilon_{Hb}^{\lambda 1}}{\varepsilon_{Hb}^{\lambda 1} - \varepsilon_{HbO2}^{\lambda 1}} \quad \text{(Equation 19a)}$$

$$\beta = \frac{-\varepsilon_{HbO2}^{\lambda 2}}{\varepsilon_{Hb}^{\lambda 1} - \varepsilon_{HbO2}^{\lambda 1}} \quad \text{(Equation 19b)}$$

$$\Phi = \frac{\Delta OD^{\lambda 1}}{\Delta OD^{\lambda 2}} \quad \text{(Equation 19c)}$$

As is clear from the rightmost side in the Equation 18, it can be seen that the value of SaO2 is given as a function proportional to the parameter Φ. The parameter Φ is a ratio between the amplitudes of the pulse waveforms measured at the waveform λ1 and the waveform λ2 as in the Equation 19c. The parameters α and β can be theoretically calculated from the Equation 19a and the Equation 19b, or the photoabsorption coefficients of hemoglobin as illustrated in FIG. 4, but in many cases, are required to be calibrated based on the transformation table obtained by previous experiments. This is because by doing so, a divergence between the condition under which the Lambert-Beer law is established and the actual condition in the living body can be corrected.

The method is an operation principle of the pulse oximeter, and the pulse oximeter uses the measurement results with two wavelengths thereby to calculate arterial oxygen saturation SpO2.

First Embodiment

Structure of Measurement Device

Figure 6:
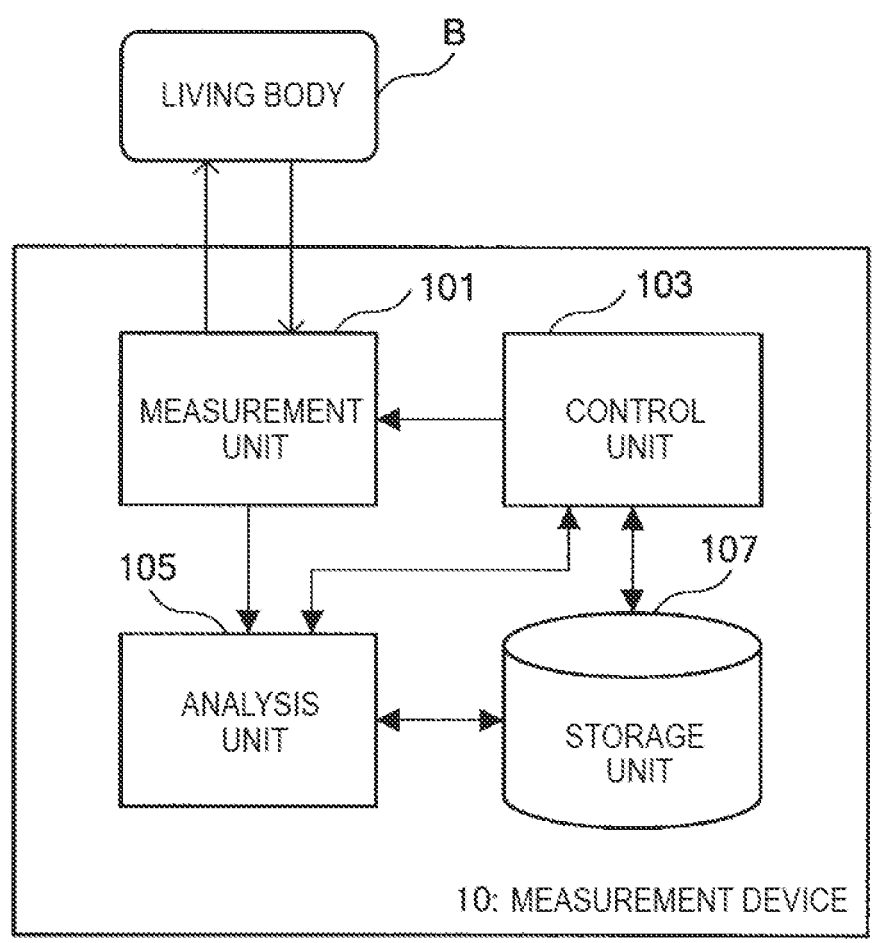
FIG. 6 is a block diagram illustrating an exemplary structure of a measurement device according to a first embodiment of the present disclosure.
Figure 7:
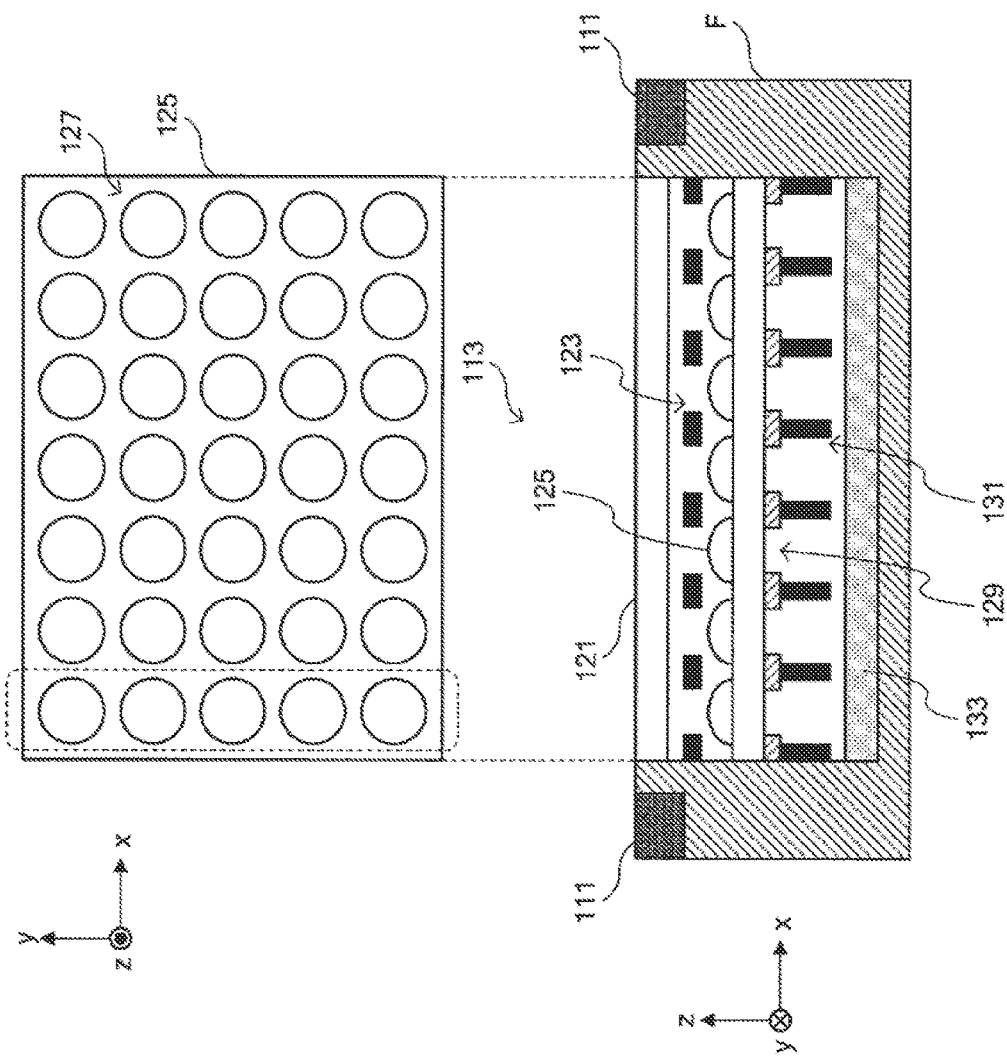
FIG. 7 is an explanatory diagram illustrating an exemplary measurement unit provided in the measurement device according to the embodiment.
Figure 8:
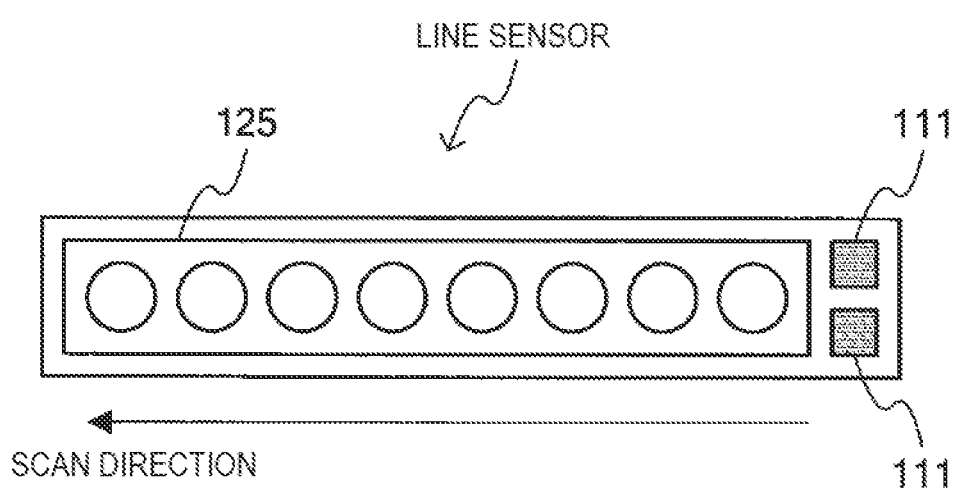
FIG. 8 is an explanatory diagram illustrating the exemplary measurement unit provided in the measurement device according to the embodiment.

Subsequently, a measurement device and a measurement method according to a first embodiment of the present disclosure will be described in detail with reference to FIG. 6 to FIG. 12. FIG. 6 is a block diagram illustrating a structure of a measurement device 10 according to the present embodiment. FIG. 7 to FIG. 9 are explanatory diagrams illustrating an exemplary measurement unit provided in the measurement device 10 according to the present embodiment. FIG. 10 to FIG. 12 are explanatory diagrams for explaining the measurement device 10 according to the present embodiment.

At first, an entire structure of the measurement device 10 according to the present embodiment will be described in detail with reference to FIG. 2.

The measurement device 10 according to the present embodiment measures at least part of a living body B as a measurement target by use of light with a predetermined wavelength, and specifies a measurement position for measuring information on pulsation along with activities of the living body from a measurement region based on the acquired measurement result. The measurement device 10 according to the present embodiment can calculate information on pulsation along with activities of the living body (such as information on pulse waveforms, information on oxygen saturation, or information capable of secondarily calculated from the information) by use of the acquired measurement result.

The measurement device 10 mainly includes a measurement unit 101 for measuring a measurement region in the living body B, a control unit 103, an analysis unit 105 and a storage unit 107 as illustrated in FIG. 6.

[Measurement Unit 101]

At first, a structure of the measurement unit 101 according to the present embodiment will be specifically described with reference to FIG. 7 to FIG. 9. The measurement unit 101 according to the present embodiment is configured of a light source 111 and a detection unit 113 as illustrated in FIG. 7.

Light Source

The light source 111 emits at least one kind of measurement light belonging to a predetermined waveform band toward a measurement region of the living body B. The light source 111 is arranged in a predetermined frame F such that the emission face of measurement light opposes the living body B.

A wavelength of measurement light emitted from the light source 111 can be set depending on an in vivo component of interest as needed, and for example, near-infrared light with a waveform of around 940 nm can be used for measuring oxygenated hemoglobin and red light with a waveform of around 660 nm can be used for measuring reduction hemoglobin. The light source 111 emits the light with wavelengths of 940 nm and 950 nm thereby to know fat present in the subcutaneous tissues. The light source 111 emits the light with wavelengths of 568 nm, 580 nm, 660 nm and 890 nm thereby to know melanin pigment. The light source 111 emits light with a wavelength of 1400 nm to 2200 nm thereby to know glucose. The light with a plurality of wavelengths is emitted from the light source 111 in a time division manner, for example.

Various wavelengths described above are merely exemplary, and the light emitted from the light source 111 in the measurement device 10 according to the present embodiment is not limited to the above examples.

The light source 111 may use a light emitting diode (LED), a small-sized laser, or the like, for example, and one or a plurality of such light emitting devices are provided for the light source 111.

The light source 111 is controlled by the control unit 103 described later in terms of an emission timing of the measurement light, an intensity of measurement light to be emitted, and the like.

A shape of the frame F in which the light source 111 is arranged is not particularly limited, but a wall as illustrated in FIG. 7 is provided between the light source 111 and the detection unit 113 described later so that the wall can be employed as a light shielding wall for preventing light emitted from the light source 111 from entering the detection unit 113.

Detection Unit

The detection unit 113 provided in the measurement device 10 according to the present embodiment regularly arranges a plurality of sensors in a predetermined arrangement therein, and is directed for detecting measurement light emitted from the light source 111 and passing through the living body B with the sensors. In other words, the detection unit 113 according to the present embodiment is configured of a so-called multi-tap sensor. FIG. 7 illustrates a sensor utilizing a micro lens array (MLA) as an exemplary detection unit 113.

The detection unit 113 provided in the measurement device 10 according to the present embodiment mainly includes a transparent substrate 121 capable of transmitting light with a wavelength band to which measurement light emitted from the light source 111 belongs, a first light shield 123, a micro lens array 125, a second light shield 129, an aperture (diaphragm) 131 and a sensor 133, for example, as illustrated in FIG. 7.

The transparent substrate 121 is where part of the living body B to be measured is arranged. The transparent substrate 121 is formed of a substrate capable of transmitting light with a wavelength used in the measurement processing. When measurement light emitted from the light source 111 and passing inside the living body B passes through the transparent substrate 121, its directivity is controlled by the first light shield 123.

The first light shield 123 functions as a directivity control plate for controlling directivity of measurement light passing through the transparent substrate 121, and is provided at a boundary between mutually adjacent micro lenses 127 in the micro lens array 125 described later. The first light shield 123 is provided so that directivity of measurement light incident into each micro lens 127 can be controlled, which enables more accurate measurement. The measurement light passing through the first light shield 123 is guided to the micro lens array 125.

The micro lens array 125 is configured of a plurality of micro lenses 127 as light receiving lenses as illustrated in the upper part of FIG. 7, and each micro lens 127 is arranged in the x direction and in the y direction on a predetermined substrate in a grid shape. Each micro lens 127 guides measurement light incident into the micro lens 127 to the sensor 133 described later. The micro lens array 125 has less curvature of field and has no distortion in the depth direction. Such a micro lens array 125 is used thereby to acquire better measurement data. Even if the living body B is present within the close-up distance, a depth of field of each micro lens 127 configuring the micro lens array 125 is set to cover the skin structure of interest (to focus up to a depth of several millimeters to several tens of millimeters from the body surface, for example) by the measurement device 10 according to the present embodiment.

The number of micro lenses 127 arranged in the micro lens array 125 according to the present embodiment is not limited to the example illustrated in the upper part of FIG. 7. The number of micro lenses 127 arranged in the micro lens array 125 according to the present embodiment can be freely set depending on a size of a living body to be shot or a size of the sensor 133.

Measurement light incident into the micro lens array 125 is focused into the micro lenses 127 to be image-formed to the sensor 133 described later.

Herein, the second light shield 129 is provided at a boundary between mutually adjacent micro lenses 127 at the face of the micro lens array 125 on the sensor 133 side. The second light shield 129 and the aperture (diaphragm) 131 enables directivity of measurement light passing through the micro lens array 125 to be controlled, and enables light incident into each micro lens 127 to be separated from light incident into an adjacent micro lens 127. Thereby, the measurement device 10 according to the present embodiment can select measurement light focused into the sensor 133.

The measurement device 10 according to the present embodiment is provided with various light shields or aperture as described above so that an incidence angle of light incident into each micro lens 127 is restricted, thereby preventing crosstalk between the micro lenses 127 caused by body scattering. Crosstalk between the micro lenses 127 is prevented thereby to acquire a signal obtained from sensor pixels corresponding to some micro lenses 127 among the micro lenses 127 provided in the micro lens array 125 (or a signal corresponding to a local position in the measurement region), thereby enhancing a temporal resolution and a spatial resolution of data measured by the sensor 133 described below.

The sensor 133 detects an intensity of measurement light at each position in the xy plane illustrated in the upper part of FIG. 7. The sensor 133 converts an intensity of measurement light received by a photo detector (PD) or the like into an electric signal to be output to the analysis unit 105 described later. The sensor 133 may employ a 2D area sensor such as photodiode, CCD (Charge Coupled Devices) image sensor, CMOS (Complementary Metal Oxide Semiconductor) image sensor, sensor using organic EL as light receiving device, or TFT (Thin Film Transistor) image sensor. The measurement device 10 may be mounted with a 1D sensor such as line sensor in the x axis direction as a simplified model on the sensor as shown in FIG. 8.

One or a plurality of pixels are arranged below one micro lens 127, and when a plurality of pixels are provided corresponding to one micro lens 127, the control unit 103 or software described later controls such that an invalid pixel caused by a distance between the micro lens 127 and the subject is not present.

The sensor 133 is controlled by the control unit 103 described later in terms of scan timing and the like, and can output a detection intensity at any position in the upper part of FIG. 7 to the analysis unit 105, for example.

The structure of the measurement unit 101 according to the present embodiment has been described above in detail with reference to FIG. 7 and FIG. 8.

Data to be Measured by Measurement Unit

Data (measurement data) to be measured by the measurement unit 101 according to the present embodiment will be described below in detail with reference to FIG. 9.

As described with reference to FIG. 1, the human skin can be classified into three of epidermic layer, dermic layer and subcutaneous fat from the skin surface. The three regions are different in optical properties, and are mutually different in thicknesses. As is clear from the fact that a scattering coefficient of the dermis is around 27 $mm^{-1}$ and a scattering coefficient of fat is around 12.6 $mm^{-1}$, a human body is a medium which excellently scatters light. Therefore, comprehensive optical properties of the skin structure are largely different depending on a personal difference or over-time change of a ratio of thicknesses of the skin structure. Melanin pigments contained in the epidermis are one factor for reducing a light transmission rate.

Measurement light emitted from the light source 111 and incident into the living body B travels substantially in a U shape as illustrated in FIG. 9 while scattering inside the living body B, and is detected by the detection unit provided at a position. At this time, as schematically illustrated in FIG. 9, the detection unit farther away from the light source 111 can detect measurement light deeply scattered and returned to the body surface. That is, in FIG. 9, a sensor farther away from the light source 111 in the x axis direction (such as a sensor positioned on the right side in FIG. 9) can detect deeper-penetrated measurement light. A depth of measurement may be around L/2 assuming an isolation distance between the light source 111 and a sensor of interest as L. Energy with a specific wavelength of the measurement light is absorbed due to various in vivo components present on the optical path and its intensity attenuates depending on a length of a distance (optical distance) in which the light travels.

In this way, with the reflective measurement device in which a path of measurement light is substantially in a U shape, an optical depth to be searched largely varies in acquiring a blood stream variation in the arteries as an optical signal. Thus, acquisition of a good signal depends on whether a blood vessel position and a virtual depth of the blood vessel position are included in the substantially U-shaped path of the measurement light.

The measurement device 10 according to the present embodiment can independently extract a signal acquired from the sensor using a micro lens array. Thus, as described below, an output waveform from each micro lens array is analyzed thereby to accurately select a distance between the sensor corresponding to a signal with a required depth and the light source.

In the general pulse oximeters as illustrated in FIG. 2A and FIG. 2B, when a measurement is made at a finger or ear lobe, the light source and the photo detector are present at a distance of about 10 mm therebetween, and thus light from the light source is efficiently diffused at the finger or ear lobe. The photo detector measures only a result added with areal spread. The thus-obtained measurement data is a factor causing a large deterioration in resolution in the temporal axis direction. On the other hand, in a reflective device such as the measurement device 10 according to the present embodiment, a distance from an object to be measured can be reduced to several millimeters, and the measurement device 10 according to the present embodiment can detect a change in minuter region in the MLA optical system. The sites in a living body used as measurement regions include a site where good measurement data (such as good pulse waveforms) can be acquired and an invalid region where an artery is not present depending on a region, but the measurement device 10 according to the present embodiment can independently acquire signals acquired from many micro lenses and use them for processing, and thus the analysis unit 105 and the control unit 103, which will be described later, are mutually cooperate thereby to automatically adjust a difference in blood vessel position. Thereby, the measurement device 10 according to the present embodiment can extract a pulse waveform with a remarkably high temporal resolution.

Light with a plurality of wavelengths may be used as measurement light depending on information on pulsation along with activities of a living body of interest, such as oxygen saturation, but it is known that an optically invadable depth into the human skin is different between infrared light and red light, for example. For example, light with a wavelength of 700 to 1000 nm is mainly scattered, but visible light or light with a wavelength of 1000 nm or more is mainly absorbed and thus the light deeply enters the living body with difficulty. Thus, for example, red light with a wavelength of 660 nm has a property of returning to the sensor via a shallower part than the infrared light (near-infrared light) with a wavelength of 940 nm. Consequently, also with the measurement device 10 according to the present embodiment, wavelength dependency may occur for an optimum distance from an artery in MLA. In the measurement device 10 according to the present embodiment, the analysis unit 105 described later analyzes a difference of the distance based on an amplitude of the signal from MLA, thereby enabling the MLA position for adjusting a depth different due to a wavelength to be optimized per wavelength.

[Control Unit 103]

Returning to FIG. 6, the control unit 103 provided in the measurement device 10 according to the present embodiment will be described.

The control unit 103 is realized by CPU (Central Processing Unit), ROM (Read Only Memory), RAM (Random Access Memory), or the like, for example. The control unit 103 controls to drive the light source 111, the sensor 133 and the like provided in the measurement unit 101, thereby governing the total measurement processing on the living body B in the measurement unit 101. More specifically, the control unit 103 controls the driving of the sensor such as scan timing of the sensor 133 or selection of the sensor 133 for acquiring information based on a predetermined synchronization signal or the like. Further, the control unit 103 controls the driving of the light source 111 for emission timing or intensity of measurement light.

The control unit 103 controls the above driving so that the light source 111 of the measurement unit 101 can emit measurement light with a different wavelength in a time division manner and can acquire measurement data at any position on the sensor 133 in a time division manner.

Measurement data measured by the measurement unit 101 the driving of which is controlled by the control unit 103 is output to the analysis unit 105 described later, where the measurement data is analyzed.

Herein, when controlling the measurement unit 101, the control unit 103 can refer to various programs, parameters, databases and the like recorded in the storage unit 107 described later.

[Analysis Unit 105]

The analysis unit 105 provided in the measurement device 10 according to the present embodiment is realized by CPU, ROM, RAM or the like, for example. The analysis unit 105 performs an analysis processing of specifying a measurement position for measuring information on pulsation along with activities of a living body from a measurement region based on a temporal change in the amount of light of the detected measurement light by use of a detection result detected by the detection unit 113 in the measurement unit 101.

With the general measurement devices illustrated in FIG. 2A and FIG. 2B, a group of temporal changes due to blood stream observed in each veinule in a fingertip or ear lobe is analyzed by extracting only a result added by one sensor. Thus, the following drawbacks are caused with the general measurement devices as illustrated in FIG. 2A and FIG. 2B.

Deterioration in signal to noise ratio (S/N) along with signal addition in region where invalid venous blood is present or in region where less arteries are distributed Deterioration in signal waveform due to added (combined) waveforms different in temporal phase Deterioration in temporal resolution of waveform due to integral addition of wide range of data On the other hand, the measurement device 10 according to the present embodiment can select and acquire signals with various waveforms for different measurement sites from a sensor pixel corresponding to each micro lens by use of a micro lens array optical system as an optical system of the measurement unit 101. The analysis unit 105 according to the present embodiment performs the following processing by use of the fact that an isolation distance between each micro lens and the light source is largely correlated with a returning depth (or measurement depth) due to subcutaneous reflective scattering.

To acquire proper pulse waveform data acquired from change in blood stream in minute region To adjust proper data acquisition position depending on blood vessel position or depth different per person To individually analyze effect due to change in depth of returning light different per wavelength, and to acquire change in luminance of pulsation from accurate position The analysis unit 105 according to the present embodiment combines the waveform results in the minute regions, thereby acquiring a better pulse waveform.

When a periodical component such as pulsation is to be found, the analysis unit 105 according to the present embodiment selects a signal from a micro lens position where maximum amplitude of a pulse waveform can be acquired. On the other hand, the waveform may not be proper with the method, and thus the analysis unit 105 can use the following method in order to find an optimum waveform.

The measurement device 10 according to the present embodiment can individually acquire and use data (data in a minute region in a measurement region) acquired from a pixel corresponding to each micro lens as described above. The analysis unit 105 specifies, from a measurement region, a measurement position for measuring information on pulsation along with activities of a living body (which will be simply denoted as pulsation information below) in terms of a temporal change in data in a minute region acquired from a pixel (or group of pixels) corresponding to each micro lens.

That is, the analysis unit 105 according to the present embodiment can calculate pulse waveform data in a minute region of interest in terms of a temporal change in data in the minute region. The analysis unit 105 uses a previously measured pulse waveform (such as data measured by other measurement device or the like) to calculate a degree of similarity between the previously measured pulse waveform and pulse waveform data in each minute region. The analysis unit 105 may calculate a correlation coefficient as an evaluation value indicating a degree of similarity between two waveforms, or may calculate a sum of absolute difference (SAD), a sum of squared difference (SSD) or the like. When the calculated degree of similarity is a predetermined threshold or more (that is, it is determined that the two waveforms are similar), the analysis unit 105 can specify the minute region giving the degree of similarity as a measurement position suitable for measuring pulsation information.

Thereby, the analysis unit 105 can automatically specify a measurement position suitable for measurement depending on a type of pulsation information of interest such as a set of minute regions giving proper amplitude of a pulse waveform or a set of minute regions giving a proper pulse waveform. The set of minute regions giving proper amplitude of a pulse waveform can be used as a helpful measurement position when a heart rate of a living body is specified based on a measurement result by the measurement device 10, for example. The set of minute regions giving a proper pulse waveform can be used as a helpful measurement position when knowledge on pulsation information other than the heart rate is acquired.

The analysis unit 105 according to the present embodiment can select data when the measurement data output from the measurement unit 101 is used for the processing based on the information on the measurement position suitable for acquiring the thus-acquired pulsation information. Further, the analysis unit 105 according to the present embodiment may feed the thus-acquired information on the measurement position back to the control unit 103. Thereby, the control unit 103 can efficiently control the measurement unit 101.

As described before, the measurement position suitable for acquiring pulsation information can change depending on a wavelength of light used as a light source, but the analysis unit 105 according to the present embodiment performs the analysis processing per wavelength of light used as a light source, and thus a measurement position suitable for acquiring pulsation information can be specified per wavelength of measurement light.

Figure 10A:
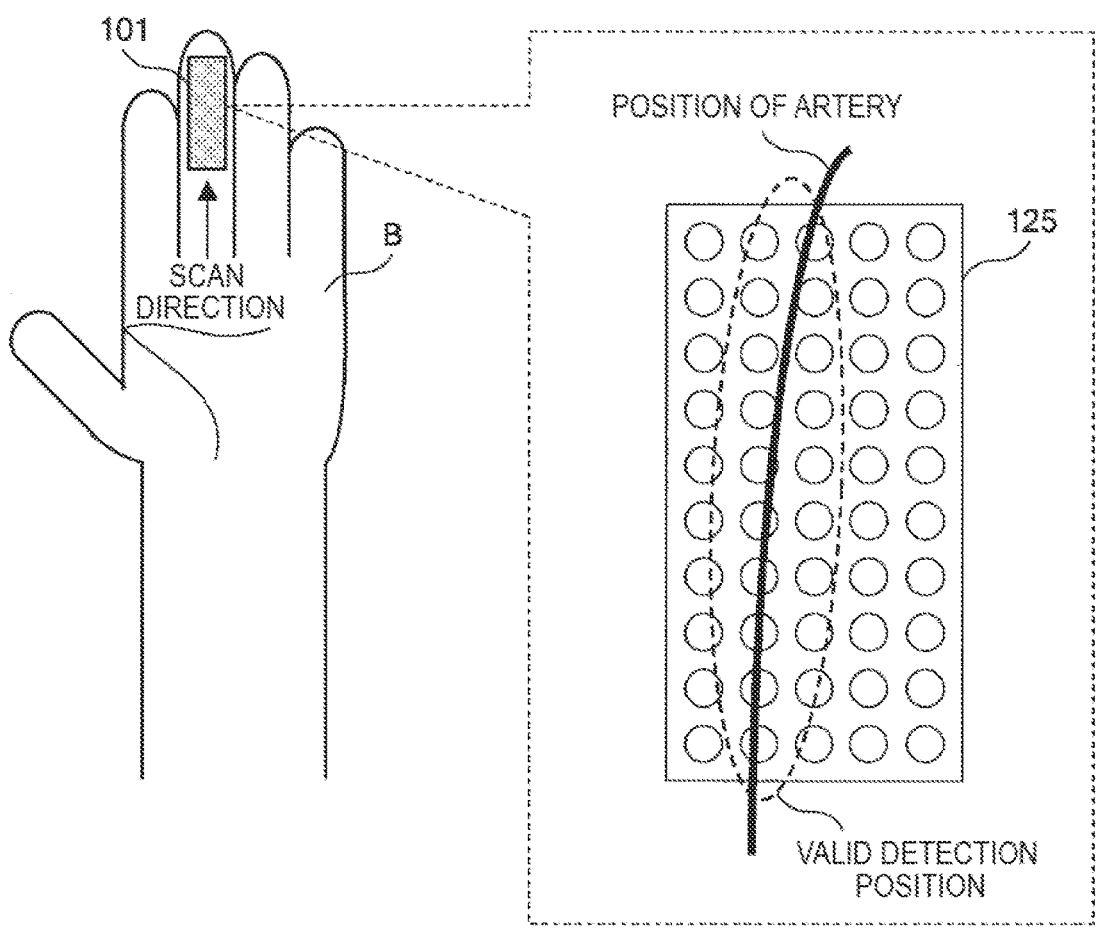
FIG. 10A is an explanatory diagram for explaining the measurement device according to the embodiment.
Figure 10B:
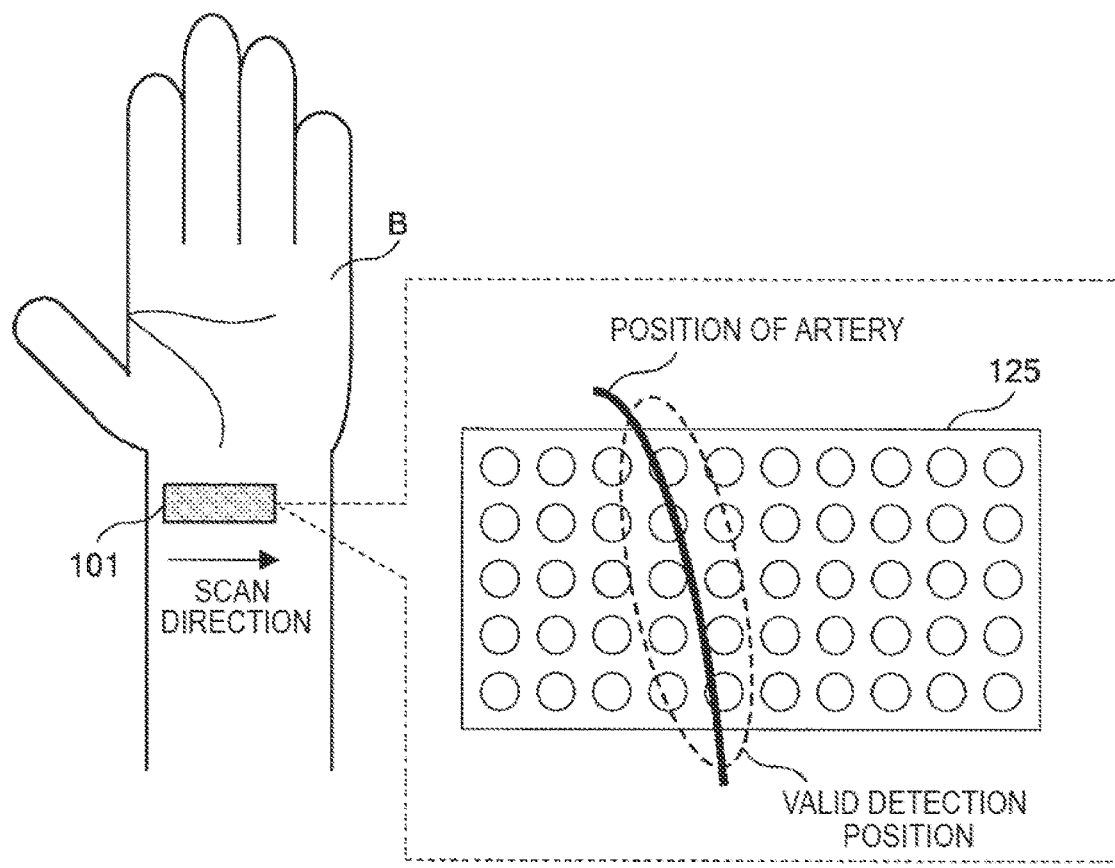
FIG. 10B is an explanatory diagram for explaining the measurement device according to the embodiment.

In this way, the measurement device 10 according to the present embodiment can automatically adjust a measurement position for acquiring pulsation information by the analysis processing on the measurement position by the analysis unit 105 according to the present embodiment. Consequently, for example, even when a measurement region is a finger as illustrated in FIG. 10A or even when a measurement position is where arteries are present in only part of a wide measurement region as illustrated in FIG. 10B, a valid measurement region can be automatically specified. Consequently, the measurement device 10 according to the present embodiment can make proper measurements even when a living body is not contacted on a specific position of the measurement device 10. The function of the measurement device 10 according to the present embodiment is mounted on various portable devices such as cell phone and portable tablet, thereby measuring pulsation information if the user only holds the portable device.

The analysis unit 105 according to the present embodiment performs the analysis processing by use of data at a measurement position specified as described above, thereby further calculating various items of pulsation information (such as pulse waveform itself, oxygen saturation, and information capable of being secondarily calculated from the information).

That is, the analysis unit 105 tracks a temporal transition of the light amount or luminance of light detected by the sensor in terms of a temporal change in measurement data acquired from a proper measurement position, thereby acquiring a pulse waveform derived from arterial pulsation.

Further, the analysis unit 105 can calculate the oxygen saturation SpO2 of the arterial blood based on the measurement data acquired from a proper measurement position by use of the arithmetic expressions indicated in the Equation 18 to Equation 19c.

The analysis unit 105 can further calculate secondary information such as AI value (Augmentation Index) or pulse wave velocity (PWV) by additional use of pulse waveform data acquired by the analysis processing. The method for calculating secondary information is not particularly limited, and a well-known method can be used therefor.

Further, the analysis unit 105 can measure a variety of substance concentrations by making multivariate analysis with a well-known method by use of the measurement data acquired from a proper measurement position, like the amount of components of melanin pigments or the amount of components in the blood such as glucose, albumin and cholesterol.

The analysis unit 105 according to the present embodiment may add a detection signal acquired from pixels corresponding to a group of micro lenses at substantially the same distances from the light source, thereby increasing signal intensity, as illustrated in FIG. 11, for example. As illustrated in FIG. 11, the horizontal pixels of the sensors corresponding to the positions at substantially the same distances from the light source detect the measurement data with mutually identical phases. Thus, as illustrated in FIG. 11, the detection signals acquired from the horizontal line are integrated thereby to increase signal intensity.

When a plurality of signals are integrated (in other words, a plurality of signals are combined), if a temporal axis shifts, the signals may mutually cancel and a temporal resolution can be deteriorated. Therefore, when a plurality of signals are combined, the analysis unit 105 according to the present embodiment corrects the temporal axis to match the top or bottom positions of the signal waveforms (such as pulse waveforms), and then performs a signal integration processing as illustrated in FIG. 12.

The sensors are arranged such that the vertical scan direction (or vertical synchronization direction) illustrated in FIG. 11 is perpendicular to the direction in which a plurality of light sources are arranged, thereby matching the temporal axis even with the CMOS sensors, not only with the CCDs. When the vertical scan direction is parallel with the direction in which the light sources are arranged, the pixels in the vertical direction with a different temporal axis are added and thus a temporal resolution deteriorates. Therefore, the vertical scan direction is desirably set to be perpendicular to the direction in which the light sources are arranged.

The analysis unit 105 according to the present embodiment may combine the signals with different phases (such as the signals acquired from the pixels in a different vertical scan direction in FIG. 11), not only the signals with the same phase, thereby performing various kinds of analysis processing. Also in this case, the analysis unit 105 properly corrects a temporal axis with the method described in FIG. 12, and prevents the signals from mutually canceling, thereby to perform the combination processing.

The analysis unit 105 according to the present embodiment has been described above in detail with reference to FIG. 10 to FIG. 12.

[Storage Unit 107]

Returning to FIG. 6, the storage unit 107 provided in the measurement device 10 according to the present embodiment will be described.

The storage unit 107 is realized by the RAM, a storage device, or the like provided in the measurement device 10 according to the present embodiment. The storage unit 107 stores therein data on photoabsorption spectra used for the analysis processing in the analysis unit 105, a look-up table of various databases, and the like. The storage unit 107 may store therein measurement data measured by the measurement unit 101 according to the present embodiment, various programs or parameters or items of data used for the processing performed by the control unit 103 or the analysis unit 105 according to the present embodiment, and the like. The storage unit 107 can store, in addition to the above data, various parameters, processing progresses, and the like which need to be stored for any processing of the measurement device 10, as needed. Each processing unit such as the measurement unit 101, the control unit 103 or the analysis unit 105 can freely access the storage unit 107 and can write or read data in or from the storage unit 107.

The structure of the measurement device 10 according to the present embodiment has been described above in detail with reference to FIG. 6 to FIG. 12.

As described above, with the measurement device 10 according to the present embodiment, it is possible to detect a slight signal which is difficult to capture by the reflective or transmissive pulse oximeter using a finger or ear lobe, and it is possible to detect an accurate pulse waveform with a high temporal resolution based on the slight signal.

A long-time measurement can be made at low loads with the reflective-scattering illumination system capable of measurement on either side with low loads on a person. The measurement device 10 according to the present embodiment enables automatic adjustment using a valid region of the image sensor without the need of a mechanism for strictly fixing a site to be measured such as finger. With the effects, the blood component analysis can be used for measuring a variety of substance concentrations, thereby coping with the micro components such as glucose, albumin and cholesterol.

The control unit 103 and the analysis unit 105 according to the present embodiment may be part of the measurement device 10 according to the present embodiment, or may be realized by an external device such as computer connected to the measurement device 10. Measurement data generated by the measurement unit 101 is stored in a removable storage medium and the storage medium is removed from the measurement device 10 to be connected to other device having the analysis unit 105, and thus the measurement data may be analyzed.

Heretofore, an example of the functions of the measurement device 10 according to the present embodiment has been shown. Each of the structural elements described above may be configured using a general-purpose material or a general-purpose circuit, or may be configured from hardware dedicated to the function of each structural element. Also, a CPU or the like may perform all the functions of the structural elements. Accordingly, the configuration to be used can be changed as appropriate according to the technical level at the time of carrying out the present embodiment.

Additionally, a computer program for realizing each function of the measurement device according to the present embodiment as described above can be created, and the computer program can be implemented in a personal computer or the like. A recording medium in which such computer program is stored and which can be read by a computer can also be provided. The recording medium is a magnetic disk, an optical disk, a magneto-optical disk, a flash memory, or the like, for example. Also, the computer program may be distributed via a network, for example, without using a recording medium.

(Hardware Configuration)

Figure 13:
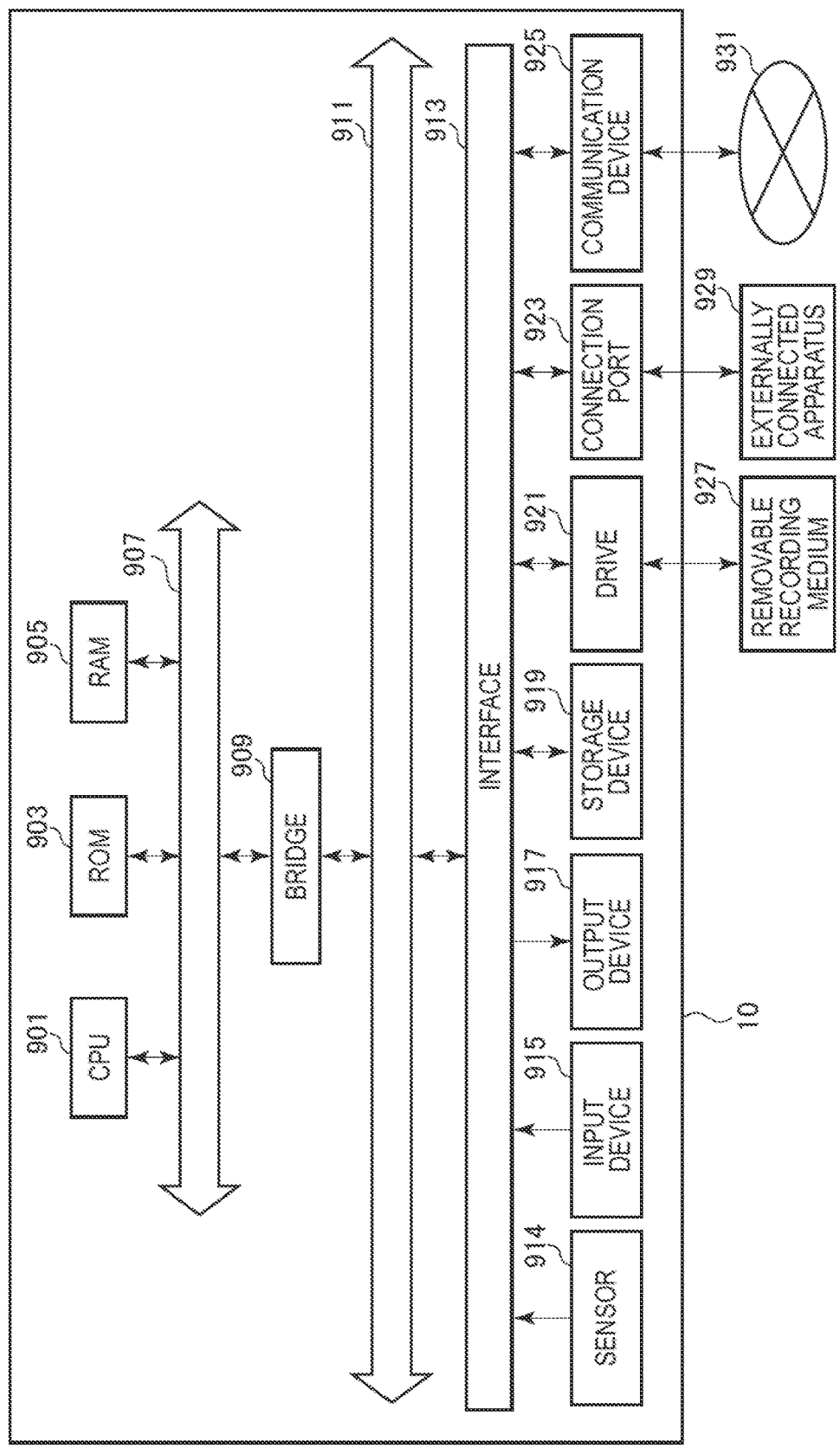
FIG. 13 is a block diagram illustrating an exemplary hardware structure of the measurement device according to the embodiment of the present disclosure.

Next, the hardware configuration of the measurement device 10 according to the embodiment of the present disclosure will be described in detail with reference to FIG. 13. FIG. 13 is a block diagram for illustrating the hardware configuration of the measurement device 10 according to the embodiment of the present disclosure.

The measurement device 10 mainly includes a CPU 901, a ROM 903, and a RAM 905. Furthermore, the measurement device 10 also includes a host bus 907, a bridge 909, an external bus 911, an interface 913, a sensor 914, an input device 915, an output device 917, a storage device 919, a drive 921, a connection port 923, and a communication device 925.

The CPU 901 serves as an arithmetic processing apparatus and a control device, and controls the overall operation or a part of the operation of the measurement device 10 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The sensor 914 is detecting means for detecting biological information unique to a user or various types of information to be used to acquire such biological information. This sensor 914 includes, for example, various imaging devices such as a CCD (Charge Coupled Device) or a CMOS (Complementary Metal Oxide Semiconductor) and the like. In addition, the sensor 914 may further have optics such as a lens to be used to image an organism site or a light source and the like. The sensor 914 may also be a microphone and the like for acquiring sound and the like. Note that in addition to those mentioned above, the sensor 914 may also include various measuring instruments such as a thermometer, an illuminance meter, a hygrometer, a speedometer, an accelerometer, and the like.

The input device 915 is an operation means operated by a user, such as a mouse, a keyboard, a touch panel, buttons, a switch and a lever. Also, the input device 915 may be a remote control means (a so-called remote control) using, for example, infrared light or other radio waves, or may be an externally connected apparatus 929 such as a mobile phone or a PDA conforming to the operation of the measurement device 10. Furthermore, the input device 915 generates an input signal based on, for example, information which is input by a user with the above operation means, and is configured from an input control circuit for outputting the input signal to the CPU 901. The user of the measurement device 10 can input various data to the measurement device 10 and can instruct the measurement device 10 to perform processing by operating this input apparatus 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processing performed by the measurement device 10. More specifically, the display device displays, in the form of texts or images, a result obtained by various processes performed by the measurement device 10. On the other hand, the audio output device converts an audio signal such as reproduced audio data and sound data into an analog signal, and outputs the analog signal.

The storage device 919 is a device for storing data configured as an example of a storage unit of the measurement device 10 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader/writer for recording medium, and is embedded in the measurement device 10 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the measurement device 10. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the measurement device 10 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the measurement device 10 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

CONCLUSION

As described above, according to the embodiment of the present disclosure, it is possible to specify a measurement position suitable for measuring information on pulsation along with activities of a living body, and it is possible to flexibly cope with a change in measurement position due to a personal difference.

Local measurement data acquired from the sensor using the micro lens array optical system is used thereby to acquire pulse waveforms with a higher temporal resolution than a general reflective or transmissive measurement device. At this time, each signal acquired from the sensor using the micro lens array is temporally corrected to be combined, thereby measuring sufficiently accurate pulse waveforms even at a fingertip.

With the measurement device according to the embodiment of the present disclosure, it is possible to automatically detect a position suitable for measurement, and thus a living body fixing member for position alignment is not required, thereby enhancing user's convenience.

Further, the measurement device according to the embodiment of the present disclosure can measure pulse waveform data excellent in a spatial resolution and a temporal resolution, and thus can cope with analyses of micro blood components such as glucose, albumin and cholesterol, not only oxygen saturation SpO2.

Furthermore, a plurality of measurement devices according to the embodiment of the present disclosure is used thereby to detect pulse waveform data at a plurality of measurement positions in a living body, which can be used for measuring central aortic blood pressure and the like.

The preferred embodiment of the present disclosure has been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

Additionally, the present technology may also be configured as below.

(1)
A measurement device including:
a light source which emits at least one kind of measurement light belonging to a predetermined wavelength band toward a measurement region formed of at least part of a living body;
a detection unit in which a plurality of sensors is regularly arranged in a predetermined arrangement and which detects the measurement light emitted from the light source and passing through the living body with the plurality of sensors; and
an analysis unit which performs analysis processing of specifying a measurement position for measuring information on pulsation along with activities of the living body from the measurement region based on a temporal change in an amount of light of the detected measurement light by use of a detection result detected by the detection unit.

(2)
The measurement device according to (1), wherein the detection unit detects measurement light passing through the living body with a sensor including a micro lens array in which a plurality of lenses is regularly arranged in a grid shape.

(3)
The measurement device according to (2), wherein a light shield for preventing crosstalk of the measurement light to be detected is provided between the micro lens array and the plurality of sensors.

(4)
The measurement device according to any one of (1) to (3), wherein the analysis unit further calculates a pulse waveform derived from arterial pulsation inside the living body corresponding to the measurement region as information on pulsation along with activities of the living body based on a temporal change in the amount of light of the measurement light.

(5)
The measurement device according to (4), wherein the analysis unit specifies the measurement position depending on a degree of similarity between the previously measured pulse waveform in the living body and the pulse waveform calculated based on a temporal change in the amount of light of the measurement light.

(6)
The measurement device according to (4), wherein the analysis unit specifies, as the measurement position, a position giving maximum amplitude of the pulse waveform calculated based on a temporal change in the amount of light of the measurement light.

(7)
The measurement device according to (5), wherein the analysis unit specifies the measurement position for measuring amplitude of the pulse waveform as information on pulsation along with activities of the living body.

(8)
The measurement device according to (5), wherein the analysis unit specifies the measurement position for measuring a shape of the pulse waveform as information on pulsation along with activities of the living body.

(9)
The measurement device according to any one of (1) to (8), wherein the analysis unit performs the analysis processing per wavelength of the measurement light emitted from the light source.

(10)
The measurement device according to any one of (4) to (9), wherein the analysis unit further calculates oxygen saturation in the arteries by use of the calculated pulse waveform.

(11)
The measurement device according to any one of (1) to (10), wherein the analysis unit corrects a phase in a temporal axis of the detection result depending on an isolation distance between a position where the measurement light is detected by the plurality of sensors and the light source.

(12)
The measurement device according to any one of (1) to (11), wherein the analysis unit integrates the detection results at detection positions at same isolation distances from the light source in the plurality of sensors.

(13)
The measurement device according to any one of (1) to (12), wherein the analysis unit corrects and combines times for the detection results corresponding to the mutually different times.

(14)
A measurement method including:
emitting at least one kind of measurement light belonging to a predetermined wavelength band toward a measurement region formed of at least part of a living body;
detecting the measurement light emitted from a light source and passing through the living body with a detection unit in which a plurality of sensors is regularly arranged in a predetermined arrangement; and performing analysis processing of specifying a measurement position for measuring information on pulsation along with activities of the living body from the measurement region based on a temporal change in an amount of light of the detected measurement light by use of a detected detection result.

(15)

A program for causing a computer communicable with a measurement device including a light source which emits at least one kind of measurement light belonging to a predetermined wavelength band toward a measurement region formed of at least part of a living body, and a detection unit in which a plurality of sensors is regularly arranged in a predetermined arrangement and which detects the measurement light emitted from the light source and passing through the living body with the plurality of sensors to achieve:

an analysis function of performing analysis processing of specifying a measurement position for measuring information on pulsation along with activities of the living body from the measurement region based on a temporal change in an amount of light of the detected measurement light by use of a detection result detected by the detection unit.

(16)

A recording medium recording a program therein, the program for causing a computer communicable with a measurement device including a light source which emits at least one kind of measurement light belonging to a predetermined wavelength band toward a measurement region formed of at least part of a living body, and a detection unit in which a plurality of sensors is regularly arranged in a predetermined arrangement and which detects the measurement light emitted from the light source and passing through the living body with the plurality of sensors to achieve:

an analysis function of performing analysis processing of specifying a measurement position for measuring information on pulsation along with activities of the living body from the measurement region based on a temporal change in an amount of light of the detected measurement light by use of a detection result detected by the detection unit.

(17)

A measurement device including:

a light source which emits at least one kind of measurement light belonging to a predetermined wavelength band toward a measurement region formed of at least part of a living body;

a detection unit which detects the measurement light emitted from the light source and passing through the living body with a sensor including a micro lens array in which a plurality of lenses is regularly arranged in a grid shape; and an analysis unit which performs analysis processing of specifying a measurement position for measuring information on pulsation along with activities of the living body from the measurement region based on a temporal change in an amount of light of the detected measurement light by use of a detection result detected by the detection unit, and calculates a pulse waveform derived from arterial pulsation inside the living body corresponding to the measurement region.

(18)

A measurement method including:

emitting at least one kind of measurement light belonging to a predetermined wavelength band toward a measurement region formed of at least part of a living body;

detecting the measurement light emitted from a light source and passing through the living body with a sensor including a micro lens array in which a plurality of lenses is regularly arranged in a grid shape; and performing analysis processing of specifying a measurement position for measuring information on pulsation along with activities of the living body from the measurement region based on a temporal change in an amount of light of the detected measurement light by use of a detected detection result, and calculating a pulse waveform derived from arterial pulsation inside the living body corresponding to the measurement region as information on pulsation along with activities of the living body based on a temporal change in the amount of light of the measurement light.

REFERENCE SIGNS LIST 10 measurement device
101 measurement unit
103 control unit
105 analysis unit
107 storage unit
111 light source
121 transparent substrate
123 first light shield
125 micro lens array
127 micro lens
129 second light shield
131 aperture (diaphragm)
133 sensor

The invention claimed is:

1. A measurement device comprising:
a light source to emit measurement light within a predetermined wavelength band, the light source being arrangeable to emit the measurement light toward a measurement region of a living body;
a detection apparatus to detect emitted measurement light, the detection apparatus being arrangeable to detect the emitted measurement light from the living body, the detection apparatus having (i) a micro lens array which includes a plurality of lenses arranged in a predetermined arrangement and which has a light incident side, (ii) a sensor device having one or more respective sensor pixels corresponding to each of a plurality of micro lenses in the micro lens array to measure an intensity of the emitted measurement light thereon, (iii) a first light shield provided on the light incident side of the micro lens array to control directivity of the emitted measurement light onto the light incident side of the micro lens array, and (iv) a second light shield and a diaphragm provided between a side of the micro lens array which is opposite to the light incident side thereof and the sensor device to control directivity of the emitted measurement light after passing through the micro lens array; and
a processing device to perform a predetermined process to specify a measurement position from the measurement region for measuring information on pulsation of the living body based respectively on a temporal change in an amount of light of the sensor pixels corresponding to each of a number of the lenses of the micro lens array as detected by the detection apparatus,
wherein the processing device during operation calculates a pulse waveform derived from arterial pulsation inside the living body corresponding to the measurement region.

2. The measurement device according to claim 1, wherein during operation the processing device specifies, as the measurement position, a position having maximum amplitude of the pulse waveform.

3. The measurement device according to claim 1, wherein during operation the processing device performs the predetermined process per wavelength of the measurement light emitted from the light source.

4. The measurement device according to claim 1, wherein during operation the processing device further calculates oxygen saturation in the arteries from the calculated pulse waveform.

5. The measurement device according to claim 1, wherein during operation the processing device corrects a phase in a temporal axis of detection results depending on an isolation distance between a position where the measurement light is detected and the light source.

6. The measurement device according to claim 1, wherein during operation the processing device integrates detection results at detection positions at same isolation distances from the light source.

7. The measurement device according to claim 1, wherein during operation the processing device corrects and combines times for detection results corresponding to the mutually different times.

8. A measurement method comprising:
emitting, by a light source, measurement light within a predetermined wavelength band toward a measurement region of a living body;
detecting, by a detection apparatus, emitted measurement light from the living body, the detection apparatus having (i) a micro lens array which includes a plurality of lenses arranged in a predetermined arrangement and which has a light incident side, (ii) a sensor device having one or more respective sensor pixels corresponding to each of a plurality of micro lenses in the micro lens array to measure an intensity of the emitted measurement light thereon, (iii) a first light shield provided on the light incident side of the micro lens array to control directivity of the emitted measurement light onto the light incident side of the micro lens array, and (iv) a second light shield and a diaphragm provided between a side of the micro lens array which is opposite to the light incident side thereof and the sensor device to control directivity of the emitted measurement light after passing through the micro lens array; and
performing, by a processing device, a predetermined process to specify a measurement position from the measurement region for measuring information on pulsation of the living body based respectively on a temporal change in an amount of light of the sensor pixels corresponding to each of a number of the lenses of the micro lens array as detected by the detection apparatus,
wherein the processing device during operation calculates a pulse waveform derived from arterial pulsation inside the living body corresponding to the measurement region.

9. A non-transitory computer readable recording medium having stored thereon a program which when executed causes a computer communicable with a measurement device, the measurement device having (i) a light source to emit measurement light within a predetermined wavelength band in which the light source is arrangeable to emit the measurement light toward a measurement region of a living body and (ii) a detection apparatus to detect emitted measurement light in which the detection apparatus is arrangeable to detect the emitted measurement light from the living body, to:
obtain a signal indicative of detected emitted measurement light from the detection apparatus; and
perform a predetermined process, based on the signal indicative of detected emitted measurement light, to specify a measurement position from the measurement region for measuring information on pulsation of the living body,
in which the detection apparatus includes (i) a micro lens array which includes a plurality of lenses arranged in a predetermined arrangement and which has a light incident side, (ii) a sensor device having one or more respective sensor pixels corresponding to each of a plurality of micro lenses in the micro lens array to measure an intensity of the emitted measurement light thereon, (iii) a first light shield provided on the light incident side of the micro lens array to control directivity of the emitted measurement light onto the light incident side of the micro lens array, and (iv) a second light shield and a diaphragm provided between a side of the micro lens array which is opposite to the light incident side thereof and the sensor device to control directivity of the emitted measurement light after passing through the micro lens array, and
in which performing of the predetermined process to specify the measurement position is based respectively on a temporal change in an amount of light of the sensor pixels corresponding to each of a number of the lenses of the micro lens array as detected by the detection apparatus,
wherein the predetermined process comprises calculating a pulse waveform derived from arterial pulsation inside the living body corresponding to the measurement region.

* * * * *